United States Patent
Tian et al.

(10) Patent No.: US 8,318,297 B2
(45) Date of Patent: Nov. 27, 2012

(54) TITANATE NANOWIRE, TITANATE NANOWIRE SCAFFOLD, AND PROCESSES OF MAKING SAME

(75) Inventors: Z. Ryan Tian, Fayeteville, AR (US); Joshua Epstein, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 963 days.

(21) Appl. No.: 12/146,139

(22) Filed: Jun. 25, 2008

(65) Prior Publication Data
US 2008/0318044 A1 Dec. 25, 2008

Related U.S. Application Data

(60) Provisional application No. 60/946,007, filed on Jun. 25, 2007, provisional application No. 60/947,067, filed on Jun. 29, 2007, provisional application No. 60/973,604, filed on Sep. 19, 2007.

(51) Int. Cl.
*B32B 3/26* (2006.01)

(52) U.S. Cl. ............... 428/304.4; 428/306.6; 428/307.3; 428/364; 428/372; 428/401; 428/402; 977/762; 977/763

(58) Field of Classification Search .................. 977/762, 977/773, 775; 428/304.4, 305.5, 306.6, 307.3, 428/312.2, 364, 372, 401, 402
See application file for complete search history.

(56) References Cited

OTHER PUBLICATIONS

Tian et al., "Large Oriented Arrays and Continuous Films of TiO2-Based Nanotubes" Journal of American Chemical Society, Sep. 2003, p. 12384-12385.*

Dong et al., "Biocompatible nanofiber scaffolds on metal for controlled release and cell colonization" Nanomedicine, Dec. 2006, p. 248-252.*
Yoshida R, Suzuki Y, Yoshikawa S., Syntheses of TiO2(B) nanowires and TiO2 anatase nanowires by hydrothermal and post-heat treatments, J Solid State Chem 178:2179-85.
Yang J, Jin Z, Wang X, Li W, Zhang J, Zhang S, et al. Study on composition, structure and formation process of nanotube Na2Ti2O4(Oh)2. Dalton Trans 20:3898 -901.
Sun X, Li Y. Synthesis and characterization of ion-exchangeable titanate nanotubes. Chem-A Eur 9:2229-38.
Chen Q, Zhou W, Du G, Peng L-M. Trititanate nanotubes made via a single alkali treatment. Adv Mater., 2002, pp. 1208 -1211, vol. 14, No. 17, Wiley-VCH Verlag GmbH & Co. KGaA, Weinheim.
Spoerke Ed, Stupp SI. Colonization of organoapatite-titanium mesh by preosteoblastic cells. J Biomed Mater Res A 3:960-9.
Hayashi K, Uenoyama K, Matsuguchi N, Sugioka Y. Quantitative analysis of in vivo tissue responses to titanium-oxide and hydroxyapatite-coated titanium alloy. J Biomed Mater Res 25:515-23.
Zhang Y, Lim CT, Ramakrishna S, Huang ZM. Recent development of polymer nanofibers for biomedical and biotechnological applications. J Mater Sci Mater Med 16:933-46.

(Continued)

*Primary Examiner* — Matthew Matzek
(74) *Attorney, Agent, or Firm* — Morris, Manning & Martin, LLP; Tim Tingkang Xia, Esq.

(57) ABSTRACT

In one aspect, the present invention relates to a synthetic nanostructure. In one embodiment, the synthetic nanostructure has a top region substantially comprising titanate nanowires, a middle region substantially comprising titanate nanoparticles and titanate nanowires, and a bottom region substantially comprising titanium, wherein some of the titanate nanowires of the top region are extending into the middle region, wherein the middle region is between the top region and the bottom region, and wherein some of the titanate nanowires of the top region are substantially perpendicular to the bottom surface of the titanium substrate. At least some of the titanate nanowires in the top region form 3D macroporous scaffolds with interconnected macropores.

15 Claims, 13 Drawing Sheets

OTHER PUBLICATIONS

Brokx RD, Bisland SK, Gariepy J. Designing peptide-based scaffolds as drug delivery vehicles. J Control Release 78:115-23.

Mao, Y., Wong, S. S., Size- and shape-dependent transformation of nanosized titanate into analogous anatase titania nanostructures, J. Am. Chem. Soc. 2006,128, 8217-8226.

Wu, D.; Liu, J.; Zhao, X.; Li, A.; Chen, Y.; Ming, Sequence of events for the formation of titanate nanotubes, nanofibers, nanowires and nanobelts, N. Chem. Mater. 2006, 18, 547-553.

Izawa, H.; Kikkawa, S.; Koizumi, M., Ion exchange and dehydration of layered titanates, Na2Ti3O7 and K2Ti4O9, J. Phys. Chem. 1982, 86, 5023-5026.

Sun, Y.; Ndifor-Angwafor, N. G.; Riley, D. J.; Ashfold, M. N. R., Synthesis and photoluminescence of ultra-thin ZnO nanowire/nanotube arrays formed by hydrothermal growth, Chem. Phys. Lett. 2006, 431, 352-357.

Kong, X-Y.; Ding, Y.; Yang, R.; Wang, Z. L., Single-crystal nanorings formed by epitaxial self-coiling of polar nanobelts, Science, 2004, 303, 1348-1351.

Armstrong, A. R. et al, TiO2-B Nanowires, Angew. Chem. Int. Ed., 2004, pp. 2286-2288, Wiley-VCH Verlag GmbH & Co. KGaA, Weinheim.

Dong et al., Multifunctional, Catalytic Nanowire Membranes and the Membrane-Based 3D Devices, The Journal of Physical Chemistry B Letters, 2006, pp. 16819-16821, American Chemical Society.

Bhattarai et al., Alginate-Based Nanofibrous Scaffolds: Structural, Mechanical and Biological Properties, Adv. Mater., 2006, pp. 1463-1467, vol. 18 Wiley-VCH Verlag GmbH & Co. KGaA, Weinheim.

Wang, P.; Zakeeruddin, S. M.; Moser, J. E.; Nazeeruddin, M. K.; Sekiguchi, T.; Gratzel, M., A stable quasi-solid-state dye-sensitized solar cell with an amphiphilic ruthenium sensitizer and polymer gel electrolyte, Nature Materials, pp. 402-407, vol. 2, Jun. 2003.

Hagfeldt, A.; Gratzel, M., Light-induced redox reactions in nanocrystalline systems, Chem. Rev. 1995, 95, 49-68.

Paulose, M.; Shankar, K.; Yoriya, S.; Prakasam, H. E.; Varghese, O. K.; Mor, G. K.; Latempa, T. A.; Fitzgerald, A.; Grimes, C. A., Anodic growth of highly ordered TiO2 nanotube arrays to 134 μm in length, J. Phys. Chemistry Letters, 2006, 110, 16179-16184.

Miao, Z.; Xu, D.; Ouyang, J.; Guo, G.; Zhao, X.; Tang, Y., Electrochemically induced sol-gel preparation of single-crystalline TiO2 nanowires, Nano Letters, 2002, vol. 2, No. 7, 717-720.

Sander, M.; Cote, M. J.; Gu, W.; Kile, B. M.; Tripp, C. P., Template-assisted fabrication of dense, aligned arrays of titania nanotubes with well-controlled dimensions on substrates, Adv. Mater. 2004, 16, No. 22, Nov. 18.

Tian, Z. R.; Voigt, J. A.; Liu, J.; Mckenzie, B.; Xu, H., Large oriented arrays and continuous films of TiO2-based nanotubes, J. Am. Chem. Soc., 2003, 125, 12384-12384-12385.

Shchukin, D. G.; Zheludkevich, M.; Yasakau, K.; Lamaka, S.; Ferreira, M. G. S.; Mohwald, H., Layer-by-layer assembled nanocontainers for self-healing corrosion protection, Adv. Mater. 2006, 18, 1672-1678.

Horvath, E.; Kukovecz, A.; Konya, Z.; Kiricsi, I., Hydrothermal conversion of self-assembled titanate nanotubes into nanowires in a revolving autoclave, Chem. Mater. 2007, 19, 927-931.

Yada, M.; Inoue, Y.; Uota, M.; Torikai, T.; Watari, T.; Noda, I.; Hotokebuchi, T., Plate, wire, mesh, microsphere, and microtube composed of sodium titanate nanotubes on a titanium metal template, Langmuir 2007, 23, 2815-2823.

Cheung, K. Y.; Yip, C. T.; Djurisic, A. B.; Leung, Y. H.; Chan, W. K., Long k-doped titania and titanate nanowires on ti foil and fluorine-doped tin oxide/quartz substrates for solar-cell applications, Adv. Funct. Mater. 2007, 17, 555-562.

Gong, D.; Grimes, C. A.; Varghese, O. K.; Hu. W.; Singh, R. S.; Chen, Z.; Dickey, E., Titanium oxide nanotube arrays prepared by anodic oxidation, J. Mater. Res., vol. 16, No. 12, Dec. 2001.

Huang, H.; Pan, S.; Lu, F., Surface electrochemical impedance in situ monitoring of cell-cultured titanium with a nano-network surface layer, Scripta Materialia 53 (2005) 1037-1042.

Andersson, S.; Wadsley, A.D., The Structure of Na2Ti6O13 and the Alkali Metal Titanates, Acta Cryst., 1962, 15, 194-201.

Chen Q., et al., The Structure of Tritranate Nanotubes, Acta Crystallograohica, Section B, 2002, 58, 587-593.

Feist, T. P.; Davies, P.K., The Soft Chemical Synthesis of T1O2 (B) from Layered Titanates, Journal of Solid State Chemistry, 1992, 275-295, 101, Academic Press Inc.

Jorge A. Ibanez, et al., Photocatalytic Bactericidal Effect of TiO2 on Enterobacter Cloacae Comparative Study With Other Gram (−) Bacteria, Journal of Photochemistry and Photobiology, 2003, 81-85, 157.

Gabriel A. Silve, et al., Selective Differentiation of Neural Progentior Cells by High-Epitope Density Nanofibers, Science, 2004, 1352-1355, 303, American Assocaiation for the Advancement of Science.

Molly M. Stevens et al., In vivo Engineering of Organs: The bone bioreactor, Proceedings of the National Academy of Scienes of the United States of America, Aug. 9, 2005, 1145-11455, 102.

Suh, J.-K. Francis; Matthew, Howard W.T., Application of Chitosan-based polysaccharide biomaterials in caltilage tissue engineering: a review, Biomaterials, 2000, 2589-2598, 21.

Tuzlakoglu, K. et al., Nano- and micro-fiber combined scaffolds: A new architecture for bonet tissue engineering, Journal of Materials Science: Materials in Medicine, 2005, 1099-1104, 16.

Shmuel Yaccoby et al., Inhibitory Effects of Soteoblasts and Increased Bone Formation on Myeloma in Novel Culture Systems and a Myelomatus Mouse Model, The Hematology Journal, 2006, 91(2), 192-199.

* cited by examiner

TITANATE NANOWIRE, TITANATE NANOWIRE SCAFFOLD, AND PROCESSES OF MAKING SAME

CROSS-REFERENCE TO RELATED PATENT APPLICATION

This application claims the benefit, pursuant to 35 U.S.C. §119(e), of U.S. provisional patent application Ser. Nos. 60/946,007, filed Jun. 25, 2007, entitled "MULTIFUNCTIONAL NANOWIRE-BIOSCAFFOLDS ON TITANTIUM," by Z. Ryan Tian, 60/947,067, filed Jun. 29, 2007, entitled "PROCESSES FOR PREPARING NANOWIRE SCAFFOLDS ON METALLIC SUBSTRATES AND USES OF THE SCAFFOLDS" by Z. Ryan Tian and Joshua Epstein, and 60/973,604, filed Sep. 19, 2007, entitled "PROCESSES FOR PREPARING NANOWIRE SCAFFOLDS ON METALLIC SUBSTRATES AND USES OF THE SCAFFOLDS, by Z. Ryan Tian, which are incorporated herein by reference in their entireties, respectively.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited, whether discussed or not, in this specification are incorporated herein by reference in their entireties and to the same extent as if each reference was individually incorporated by reference. In terms of notation, hereinafter, "[n]" represents the nth reference cited in the reference list. For example, [28] represents the 28th reference cited in the reference list, namely, Dong, W.; Zhang, T.; McDonald, M.; Padilla, C.; Epstein, J.; Tian, Z. R. Nanomedicine. 2006, 2, 248-252.

FIELD OF THE INVENTION

The present invention relates generally to synthetic nanostructures and in particular to titanate nanowires, titanate nanowires scaffolds, methods of making same, and applications of same.

BACKGROUND OF THE INVENTION

In biomaterial science a longstanding challenge has been to make a bioscaffold that is both macroporous and mechanically tough. Natural extracellular matrix is generally too fragile to support weight. In contrast, smooth coatings on implantable metals typically can withstand the rigors of weight, but generally lack macropores to accommodate tissue growth.

One approach for providing bioscaffolds that are both durable and macroporous is by formation of a porous, ceramic nanocoatings directly on metal surfaces. A templating process or nanoseeding process may be used to form such a coating on the metal surface. Both of these processes, however, typically fail to provide scaffolds that are durable in combination with morphology that is suitable for tissue engineering. Alternatively, electrochemically corroded coating processes may be utilized. Coated metal surfaces produced by these methods, however, typically possess pores that are too small to accommodate tissue growth.

A process is needed, accordingly, for forming nanowire scaffolds on metal surfaces that may be utilized to promote cell adhesion and proliferation. A need also exists for multifunctional nanowire scaffolds produced by fabrication processes that are cost effective.

Therefore, a heretofore unaddressed need exists in the art to address the aforementioned deficiencies and inadequacies.

SUMMARY OF THE INVENTION

In one aspect, the present invention relates to a synthetic nanostructure. In one embodiment, the synthetic nanostructure has a top region substantially comprising titanate nanowires, a middle region substantially comprising titanate nanoparticles and titanate nanowires, and a bottom region substantially comprising titanium, wherein some of the titanate nanowires of the top region are extending into the middle region, wherein the middle region is between the top region and the bottom region, and wherein some of the titanate nanowires of the top region are substantially perpendicular to the bottom surface of the titanium substrate. At least some of the titanate nanowires in the top region form 3D macroporous scaffolds with interconnected macropores.

In one embodiment, the bottom region comprises a titanium substrate that is selected from the group consisting of commercially pure titanium, a titanium alloy, and a titanium compound. The titanium substrate can have a variety of shapes and sizes.

In another aspect, the present invention relates to a process for preparing a synthetic nanostructure. In one embodiment, the process includes contacting a titanium substrate with a hydroxide solution, and hydrothermally heating the titanium substrate and the hydroxide solution to a temperature of not less than about 180° C. for a time sufficient to allow a plurality of titanate nanowires to grow in the hydroxide solution both upwardly and downwardly, wherein some of the plurality of titanate nanowires are extending into a middle region between a top region comprising hydroxide solution and a bottom region comprising solid titanium. At least some of the titanate nanowires in the top region form 3D macroporous scaffolds with interconnected macropores.

In yet another aspect, the present invention relates to a process for preparing a plurality of titanate nanowires. In one embodiment, the process includes contacting a substrate comprising titanium with a hydroxide solution, and hydrothermally heating the titanium substrate and the hydroxide solution to a temperature of not less than about 180° C. for a time sufficient to form a plurality of titanate nanowires. The plurality of titanate nanowires self assembles to form 3D macroporous scaffolds with interconnected macropores.

In a further aspect, the present invention relates to a synthetic nanostructure. In one embodiment, the synthetic nanostructure has a plurality of titanate nanowires formed on a titanium substrate, wherein at least some of the plurality of titanate nanowires form 3D macroporous scaffolds with interconnected macropores.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
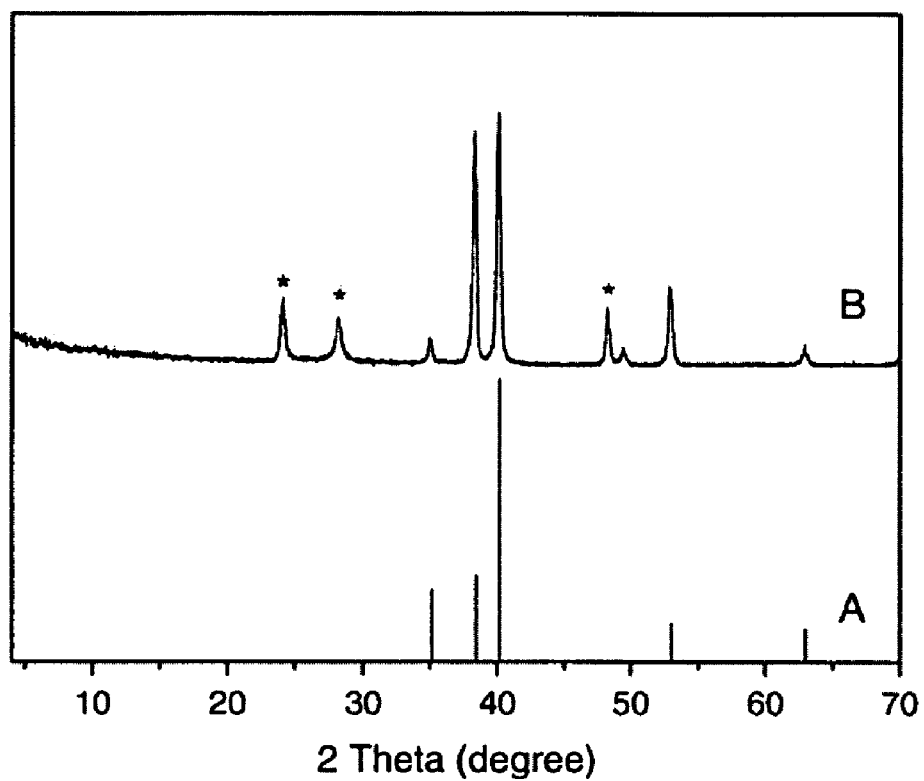
FIG. 1 depicts a graph of the x-ray diffraction (XRD) patterns of nanowire scaffold on Ti foil. (A) Ti foil. (B) Titanate nanowire scaffold on Ti foil (star-denoted peaks correspond to the titanate nanowire, the other peaks are for Ti metal).

The present invention is more particularly described in the following examples that are intended as illustrative only since numerous modifications and variations therein will be apparent to those skilled in the art. Various embodiments of the invention are now described in detail. Referring to the drawings of FIGS. 1-11, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The term "nanotube" as used herein, generally refers to tubular fibers having an outer diameter of less than about 100 nm. Nanotubes are generally formed at lower reaction temperatures compared to nanowires. As illustrated in the Examples, nanotubes typically form at temperatures of less than about 160° C., while nanowires typically form at temperatures equal or greater than about 180° C.

The term "nanowire" as used herein, generally refers to solid fibers having an average diameter of less than 100 nm. The terms "nanowire," "nanofiber," and "bio nanowire" are used interchangeably herein.

The term "scaffold" as utilized herein, generally describes the 3D architecture of the plurality of nanowires formed on the metallic substrate. Representative non-limiting microscopic images of the scaffolds formed by the process of the invention are depicted in FIG. 2, FIG. 3, FIG. 6, FIG. 7, FIG. 8, and FIG. 9. The terms "scaffold," "3D scaffold," and "bioscaffold" are used interchangeably herein.

OVERVIEW OF THE INVENTION

The description will be made as to the embodiments of the present invention in conjunction with the accompanying drawings of FIGS. 1-11. In accordance with the purposes of this invention, as embodied and broadly described herein, this invention, in one aspect, relates to a synthetic nanostructure. In one embodiment, the synthetic nanostructure has a top region substantially comprising titanate nanowires, a middle region substantially comprising titanate nanoparticles and titanate nanowires, and a bottom region substantially comprising titanium, wherein some of the titanate nanowires of the top region are vertically rooted on the nanoparticles of the middle region, wherein the middle region is between the top region and the bottom region. At least some of the titanate nanowires in the top region form 3D macroporous scaffolds with interconnected macropores.

The present invention, among other things, in another aspect, discloses a process for forming a synthetic nanostructure having a plurality of nanowires on a metallic substrate. The plurality of nanowires generally form 3D scaffolds having interconnected macropores. By varying the process parameters, such as reaction temperature, reactant concentration, and reaction time, the length and diameter of the nanowires may be controlled and concomitantly, the average diameter of the macropores may also be controlled. Because the nanowire scaffolds are both durable and macroporous, as illustrated in the examples, they are useful for a variety of biomedical and industrial applications.

(I) Process for Preparing Nanowire Scaffolds

Figure 9:
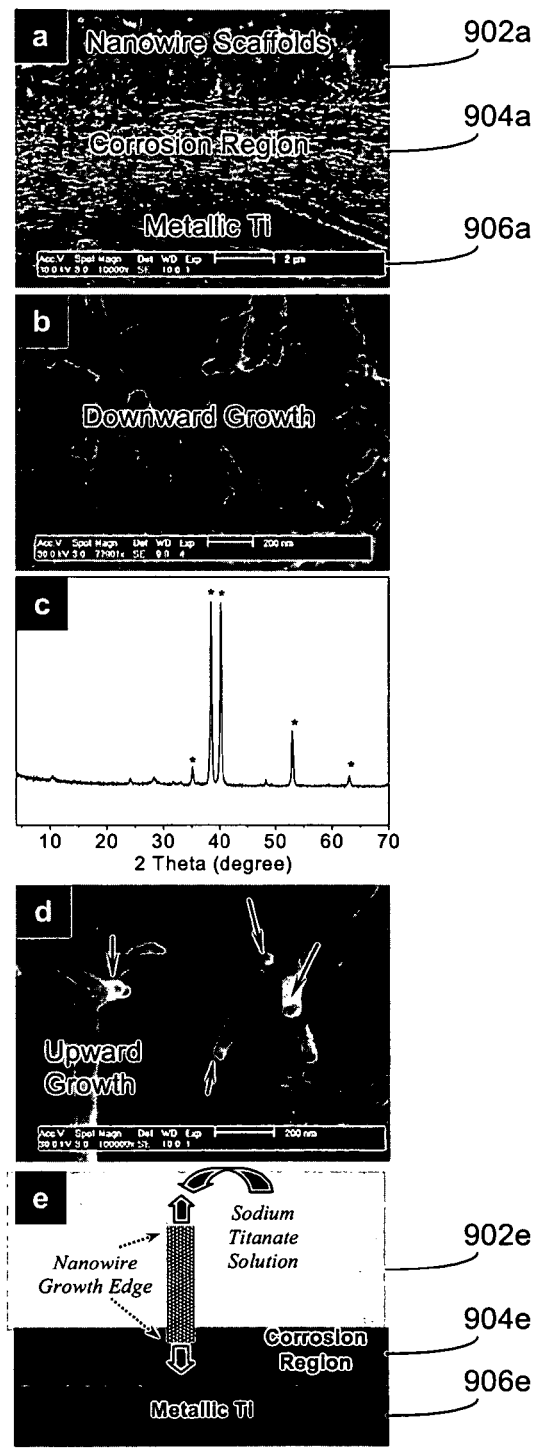
FIG. 9 depicts an SEM study on the bi-directional co-growth. (a) An SEM image from a 45° cross-section sample showing macroporous scaffolds on Ti foil. (b) The high resolution SEM picture depicts vertically oriented nanowires rooting on nanoparticles. (c) The XRD pattern of the titanate in the corrosion region on Ti (star-denoted peaks correspond to the Ti and others attribute to titanate). (d) The nanotube structures upward growth at the tip of the nanowire. (e) Schematic of a nanowire growth mechanism according to one embodiment of the present invention corresponding to the showing of (a-d).

One aspect of the present invention provides a process for preparing a plurality of nanowires on a metallic substrate. In the process, the metallic substrate is contacted with a hydroxide composition and the mixture is heated to a suitable temperature and for a time sufficient to form the plurality of nanowires. Generally speaking, the plurality of nanowires form 3D macroporous scaffolds with interconnected macropores. Three distinct regions (as shown in FIG. 9) may be microscopically visualized: a top region 902a comprising nanowires, a middle region 904a substantially comprising nanowires and nanoparticles, and a bottom region 906a substantially comprising the metallic substrate. Without being bound to any particular theory, referring to FIG. 9, it is generally believed that the plurality of nanowires self assemble via an upward and downward co-growth mechanism to form the 3D scaffolds. Each of the process parameters is discussed below.

(a) Metallic Substrate

A variety of metallic substrates are suitable for use in the present invention. As will be appreciated by a skilled artisan, the type of metallic substrate selected will greatly depend on the intended use. By way of example, when the intended use is for a biomedical purpose, the metallic substrate is typically biocompatible. Alternatively, when the intended use is for an industrial purpose, the metallic substrate may be made from a material that is not biocompatible. Non-limiting examples of suitable metallic substrates include aluminum, stainless steel, nickel, and titanium.

In an exemplary embodiment, the metallic substrate will comprise titanium. The metallic substrate may comprise commercially pure titanium. In this context, the phrase "commercially pure" means that the titanium is not alloyed with other elements. Suitable commercially pure titanium, for example, includes any of the America Society for Testing and Materials International (ASTM International) Grade 1, Grade 2, Grade 3, Grade 4, or Grade 7. Alternatively, the titanium may comprise a titanium alloy. In one alternative embodiment, the titanium alloy may be an alpha alloy. In another alternative embodiment, the titanium alloy may be a near alpha alloy. In yet another alternative embodiment, the titanium alloy may be an alpha and beta alloy. In yet another embodiment, the titanium alloy may be a beta alloy. Suitable non-limiting examples of titanium alloys include titanium-aluminum, titanium-gallium, titanium-germanium, titanium-carbon, titanium-oxygen, titanium-nitrogen, titanium-molybdenum, titanium-vanadium, titanium-tantalum, titanium-niobium, titanium-manganese, titanium-iron, titanium-chromium, titanium-cobalt, titanium-nickel, titanium-copper, and titanium-silicon. Exemplary titanium alloys include titanium-aluminum, titanium-iron, titanium-molybdenum, titanium-vanadium, and titanium-nickel. The titanium substrate may also comprise titanium compounds. Non-limiting examples of suitable titanium compounds include titanium oxide, titanium hydride, titanium nitride, and titanium carbide. The titanium substrate may also comprise a mixture of any of the foregoing materials. By way example, the titanium substrate may be a mixture of commercially pure titanium and a titanium compound. Alternatively, the titanium substrate may be a mixture of a titanium alloy and a titanium compound. By way of further example, the titanium substrate may be a mixture of one or more titanium alloys.

The size and shape of the metallic substrate can and will vary greatly without departing from the scope of the invention. For example, the morphology of the metallic substrate may be selected from foil, plate, wire, mesh, grid, sphere, and tube.

(b) Hydroxide Composition

The hydroxide composition can and will vary depending on the metallic substrate. Generally speaking, the hydroxide composition is selected such that when it is contacted with the metal substrate it will form a plurality of nanowires as described herein. For this purpose, any basic aqueous solution containing hydroxide ions may be used.

In an exemplary embodiment, the metallic substrate comprises titanium and the hydroxide composition is selected from potassium hydroxide and sodium hydroxide. In one embodiment, the hydroxide composition is potassium hydroxide. In an alternative embodiment, the hydroxide composition is sodium hydroxide.

As illustrated in the examples, one means to control the average diameter, average length, and the average diameter of the macropores is by varying the concentration of the hydroxide composition. Generally speaking, all other reaction parameters being equal, increasing the concentration of the hydroxide composition typically increases the length of the nanowires formed. For example, reactions conducted with a sodium hydroxide concentration of 0.20 mol/L will generally form nanowires that are shorter compared to nanowires produced using a sodium hydroxide concentration of 1.0 mol/L. Suitable sodium hydroxide concentrations, for example, may range from about 0.1 to about 10.0 mol/L. More typically, the concentration will be greater than about 0.2, 0.3, 0.4, 0.5, 0.6, 0.7, 0.8, 0.9, or greater than about 1.0 mol/L.

(c) Reaction Temperature

Several heating or reaction temperatures may be suitable depending upon the metallic substrate and hydroxide composition. The temperature must at least be high enough such that nanowires, as described herein, are formed. As detailed in the examples, when the metallic substrate comprises titanium, the reaction temperature must be greater than about 180° C.

for nanowires to form. When the temperature is below about 180° C., and particularly below about 160° C., it has been discovered that nanotubes form in lieu of nanowires. Accordingly, the processes of the invention are generally conducted at a temperature of not less than about 180° C. when the metallic substrate comprises titanium. Typically, the higher the temperature-the more rapidly the reaction proceeds. As such, temperatures ranging from 180° C. to about the melting point of the titanium substrate, such as about 1600° C., may be utilized to the extent the reaction vessel can accommodate the temperature without melting. More typically, the reaction temperature will range from about 210° C. to about 250° C. or from about 210° C. to about 1600° C. In other embodiments, the temperature may be greater than about 200° C., about 300° C., about 400° C., about 500° C., about 600° C., about 700° C., about 800° C., about 900° C., about 1000° C., about 1100° C., about 1200° C., about 1300° C., about 1400° C., about 1500° C., or greater than about 1600° C. As will be appreciated by a skilled artisan, certain titanium alloys have melting points well in excess of 1600° C. and for processes utilizing these alloys the reaction temperature may be increased accordingly.

Any suitable means generally known in the art may be utilized to heat the reactants (i.e., metallic substrate and hydroxide composition) to the desired temperature. In an exemplary embodiment, the reactants are hydrothermally heated as further described in the examples.

Another means to control the average diameter, average length, and the average diameter of the macropores is by varying the reaction temperature. Generally speaking, all other reaction parameters being equal, increasing the temperature typically increases the length of the nanowires formed. For example, reactions conducted at a temperature of 210° C. will generally form nanowires that are shorter compared to nanowires produced at a temperature of 240° C. The impact of temperature on the physical characteristics of the nanowires is more fully elucidated in the Examples.

(d) Reaction Time

As will be appreciated by a skilled artisan, the amount of time needed for the process of the invention to form suitable nanowires can and will vary depending upon the reactants, their concentration, and the temperature at which the reaction is conducted. Generally speaking, increasing the reaction temperature typically results in shorter reaction times. The reaction time may suitably range from about several minutes to several days or weeks. More typically, the reaction time may range from about 30 minutes to about 24 hours or from about 30 minutes to about 10 hours. In other embodiments, the reaction time may be less than about 30 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or greater than about 24 hours.

Yet an additional means to control the average diameter, average length, and the average diameter of the macropores is by varying the reaction time. Generally speaking, all other reaction parameters being equal, increasing the reaction time typically increases the length of the nanowires formed. For example, reactions conducted for 30 minutes will generally form nanowires that are shorter compared to nanowires produced with reaction times of 4 hours. The impact of reaction time on the physical characteristics of the nanowires is more fully elucidated in the Examples.

(e) Characterization of the Plurality of Nanowires

The material comprising the nanowires of the invention will greatly depend upon the composition of the metallic substrate. When the metallic substrate is aluminum, the nanowires may comprise $Al_2O_3$. Alternatively, when the metallic substrate is iron, the nanowires may comprise $Fe_2O_3$. In another embodiment, when the metallic substrate comprises nickel, the nanowires may comprise $Ni_2O_3$. In an exemplary embodiment, when the metallic substrate is titanium, it is generally believed that the nanowires substantially comprise layered hydrogen titanate having the formula $H_2TiO_{2n+1}xH_2O$. In other embodiments, the nanowires may comprise $TiO_2$—B or a mixture of $TiO_2$—B and titanate. In alternative embodiments, the nanowires will typically comprise greater than about 50% titanate, about 55% titanate, about 60% titanate, about 65% titanate, about 70% titanate, about 75% titanate, about 80% titanate, about 85% titanate, about 90% titanate, about 95% titanate, or greater than about 99% titanate (by weight).

Depending on the process parameters, the diameter and length of the nanowires may vary. The average diameter of the nanowires may range from about 1 nm to about 150 nm, and more typically, from about 10 nm to about 100 nm. In other embodiments, the average diameter of the nanowires will be greater than about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, or greater than about 120 nm.

The average length of the nanowires also can and will vary without departing from the spirit of the invention. Typically, the average length of the nanowire may range from about 1 μm to about 1 mm. More typically, the average length will range from about 1 μm to about 15 μm, or from about 5 μm to about 10 μm. In other embodiments, the average length of the nanowires is at least 1 μm, at least 2 μm, at least 3 μm, at least 4 μm, at least 5 μm, at least 6 μm, at least 7 μm, at least 8 μm, at least 9 μm, at least 10 μm, at least 20 μm, at least 30 μm, at least 40 μm, at least 50 μm, at least 60 μm, at least 70 μm, at least 80 μm, at least 90 μm, at least 100 μm, at least 200 μm, at least 300 μm, at least 400 μm, at least 500 μm, at least 600 μm, at least 700 μm, at least 800 μm, at least 900 μm, at least 10000 μm or 1 mm.

The average diameter of the interconnected macropores comprising the 3D scaffold may be varied by varying the average diameter and average length of the nanowires. For example, when the average length of the nanowires is about 5 μm, the average diameter of the macropores is from about 2 μm to about 10 μm.

(II) Uses of the Nanowire Scaffolds

Another aspect of the invention provides products and/or processes that beneficially utilize the nanowire scaffolds formed by the process of the invention. The product or process may be a biomedical application. Alternatively, the product or process may be an industrial application. Representative non-limiting examples of both biomedical and industrial applications are described in more detail below.

(a) Drug Delivery

The bioscaffolds of the invention may optionally include one or more therapeutic molecules (e.g., drugs). The bioscaffold, as such, may be used to store or deliver a drug in vivo and on-site effectively for treating a desired indication in a subject. In an exemplary embodiment, the bioscaffold may be used to deliver a drug to a targeted location, such as to an implant, a specific tissue, or organ, in the subject. In certain embodiments, the therapeutic molecule may be covalently attached to the bioscaffold. Alternatively, the therapeutic molecule may be non-covalently attached to the bioscaffold. Methods generally known in the art may be employed for conjugating the therapeutic molecule to the bioscaffold.

(i) Coated Surfaces

Generally speaking, for in vivo drug delivery, the bioscaffolds comprising the therapeutic molecule are typically coated onto a biocompatible surface by any method generally known in the art (i.e., spraying, or dip coating). Exemplary surfaces include bones, joints, and medical devices. Suitable medical devices include cardiovascular devices, such as vascular grafts and stents, dialysis and urological stents, artificial blood vessels, artificial bone joints, such as hip joints, and scaffolds that support tissue growth in such anatomical structures as nerves, pancreas, eye and muscle (as described more fully below). Other suitable medical devices include biosensors and percutaneous devices, such as catheters, that penetrate the skin and link a living body to a medical device, such as a kidney dialysis machine. The bioscaffolds may also be applied for purification, separation, collection, and storage of biological materials.

In an exemplary application, the bioscaffolds may be coated on a stent to produce a drug eluting stent. By way of example, the coated stent may be utilized to deliver to coronary arteries, cerebral vascular, central and peripheral arteries and veins, bile ducts, esophagus, colon, trachea or large bronchi, ureters, and urethra. Suitable non-limiting examples of stents suitable for use in the invention include vascular stents, urinary tract stent, CHD stent, rectal stent, oesophageal stent, biliary stent, and pancreatic stents.

The coated surfaces may be used to administer the therapeutic molecule to a subject in a time-controlled manner. The rate of drug release may be controlled by varying the size of the macropores forming the bioscaffold. Generally speaking, the therapeutic molecule is slowly released from the bioscaffold after the bioscaffold has been contacted in vivo with a subject's blood or tissue. In one embodiment, less than about 5 percent, or less than about 10 percent, or less than about 15 percent, or less than about 20 percent, or less than about 25 percent, or less than about 30 percent, or less than about 35 percent, or less than about 40 percent, or less than about 45 percent, or less than about 50 percent, or less than about 55 percent, or less than about 60 percent, or less than about 65 percent, or less than about 70 percent, or less than about 75 percent, or less than about 80 percent, or less than about 85 percent, or less than about 90 percent, or less than about 95 percent of the therapeutic molecule is released from the bioscaffold in about 24 hours after the bioscaffold has been contacted in vivo with a subject's blood or tissue. In another embodiment, the therapeutic molecule is released from the bioscaffold in a controlled release formulation over a period of about thirty days after the bioscaffold has been contacted in vivo with a subject's blood.

The concentration of therapeutic agent loaded on the bioscaffold may readily be varied to optimize the amount of drug administered to a subject. To achieve a relatively high loading of drug, the surface area of the bioscaffold is generally increased by increasing the number and volume of the macropores forming the bioscaffold.

(ii) Therapeutic Molecules

Suitable therapeutic molecules, for example, may be selected from the group consisting of anti-inflammatory agents, chemotherapeutic agents, endothelial cell migration promoting agents, angiogenesis promoting agents, anticoagulants, antibacterial agents, antiparasitic agents, antifungal agents, antiviral agents, analgesic agents, local anesthetics, and immunomodulatory agents.

In one embodiment, the therapeutic molecule is an anti-inflammatory agent. Suitable anti-inflammatory agents may be either nonsteroidal or steroidal. Nonsteroidal anti-inflammatory agents, for example, include acetylsalicylic acid, indomethacin, naproxen, and selective cyclooxygenase-2 inhibitors. Steroidal anti-inflammatory agents, for example, include hydrocortisone, and prednisone.

In another embodiment, the therapeutic molecule is a chemotherapeutic agent. Suitable chemotherapeutic agents may be selected from the group consisting of DNA synthesis inhibitors, mitotic inhibitors, antimetabolites, alkylating agents, nitrosoureas, anthracyclines, topoisomerase inhibitors, cytotoxins, anti-cytoskeletals, and angiogenesis inhibitors. Examples of DNA synthesis inhibitors include, but are not limited to, daunorubicin and adriamycin. Examples of mitotic inhibitors include paclitaxel, docetaxel, vinblastine, vincristine, and vinorelbine. Examples of antimetabolites include 5-fluorouracil, capecitabine, 6-mercaptopurine, methotrexate, gemcitabine, cytarabine (ara-C), fludarabine, pemetrexed, cytosine arabinoside, methotrexate, and aminopterin. Examples of alkylating agents include busulfan, cisplatin, carboplatin, chlorambucil, cyclophosphamide, ifosfamide, dacarbazine (DTIC), mechlorethamine, melphalan, and temozolomide. Examples of nitrosoureas include carmustine (BCNU) and iomustine (CCNU). Examples of anthracyclines include daunorubicin, doxorubicin, epirubicin, idarubicin, and mitoxantrone. Examples of topoisomerase inhibitors include topotecan, irinotecan, etoposide (VP-16), and teniposide. Examples of cytotoxins include paclitaxel, vinblastine, and macromycin. Examples of anti-cytoskeletals include taxol and cholchicine. Examples of angiogenesis inhibitors include thalidomide, angiogenic growth factor inhibitors, and matrix metalloproteinase inhibitors.

In still another embodiment, the therapeutic molecule is an anticoagulant. Suitable anticoagulants include heparin, coumarins, 1,3-indanediones, argatroban, lepirudin, and bivalirudin.

In yet another embodiment, the therapeutic molecule is an angiogenesis promoting agent. Suitable angiogenesis promoting agents include vascular endothelial growth factor (VEGF), fibroblast growth factor (FGF), interleukin-8 (IL-8), angiogenin, angiopoietin-1, angiotropin, epidermal growth factor (EGF), platelet derived endothelial cell growth factor (PDGF), granulocyte colony-stimulating factor (GCSF), transforming growth factor a (TGF-a), transforming growth factor b (TGF-b), proliferin, leptin, sphingosine 1-phospate (SIP), and nitric oxide.

In a further embodiment, the therapeutic molecule is an antibacterial agent. Suitable antibacterial agents include penicillin, cephalosporins, and bacitracin. In another embodiment, the therapeutic molecule is an antiparasitic agent. Suitable antiparasitic agents include quinacrine and chloroquine. In another embodiment, the therapeutic molecule is an antifungal agent. Suitable antifungal agents include nystatin and gentamicin. In yet another embodiment, the therapeutic molecule is an antiviral agent. Suitable antiviral agents include acyclovir, ribavirin, and interferons.

In one embodiment, the therapeutic molecule is an analgesic agent. Suitable analgesic agents include salicylic acid, acetaminophen, ibuprofen, flurbiprofen, and morphine. In another embodiment, the therapeutic molecule is a local anesthetic. Suitable local anesthetics include lidocaine, bupivacaine, and benzocaine. In yet another embodiment, the therapeutic molecule is an immunomodulatory agent. Suitable immunomodulatory agents include granulocyte colony-stimulating factor (G-CSF), interferons, imiquimod, IL-12, chemokines, synthetic cytosine phosphate-guanosine (CpG) oligodeoxynucleotides, and glucans.

In yet another embodiment, the therapeutic molecule converts an endogenous precursor form of a molecule to the active form of the endogenous molecule. Typically, the therapeutic molecule may be an enzyme that will convert an inactive agent present in the blood of a subject to an active form. Suitable enzymes, by way of non-limiting example, include sphingosine kinase, lysophosphatidic acid (LPA) acetyl transferase, phospholipase C, phospholipase A2, phospholipase D, PI3 kinase, and sphingomyelinase. The therapeutic molecule that converts an endogenous precursor form of a molecule to the active form of the molecule may also be a blood-clotting factor. Examples of activating molecules in the blood-clotting cascade include tissue factor, factor VIIa, factor Xa, and thrombin.

In an additional embodiment, the therapeutic molecule may be an agent that promotes adhesion of cells onto the bioscaffold or the surface to which the bioscaffold is coated. Typically, the agent will be a polypeptide that promotes adhesion of cells. Suitable adhesion-promoting polypeptides may be selected from the group consisting of integrins, cadherins, immunoglobulin family of cell adhesion molecules, fibronectins, laminins, selectins, mucins, proteoglycans, and fibrillin. In one exemplary embodiment, the adhesion promoting polypeptide contains an RGD moiety. In one embodiment, the adhesion promoting polypeptide containing an RGD moiety is linear. In another embodiment, the adhesion promoting polypeptide containing an RGD moiety is circular.

(b) Bioscaffold for Cell and/or Tissue Growth

The nanowire assembly of the invention may be used as a bioscaffold for cell and/or tissue growth, both in vitro and in vivo. This is because, in part, the nanowires provide both dense cellular binding sites and ample room for cells to reside and grow. Methods for growing cells and/or tissue on nanowires are described in the examples. Generally speaking, the nanowires are sterilized and then incubated under the appropriate conditions to promote cell and/or tissue growth. Sterilization techniques are well known in the art and include ultra violet radiation and ethanol. Additionally, in vitro cell culture techniques to promote cell and/or tissue growth are well known in the art. One skilled in the art would appreciate that the cell culture technique will depend, in large part, on the cell type. Typical cell culture techniques may be found, for instance, on the American Type Culture Collection website (www.atcc.org).

In one embodiment, nanowires may be used as a bioscaffold for cell growth. Generally speaking, suitable cells include cells capable of adhesion. Both eukaryotic cells and prokaryotic cells may be grown on the bioscaffold. Non-limiting examples of eukaryotic cells include vertebrate and invertebrate cells. Examples of vertebrate cells include mammalian cells, fish cells, amphibian cells, reptilian cells, and avian cells. Invertebrate cells include fungal cells, plant cells, and single-celled eukaryotic organisms. As a further example, mammalian cells may include human cells, non-human primate cells, companion animal cells (e.g. dogs and cats), agricultural animal cells (e.g. pigs, cows, sheep, llamas, alpacas, horses, and goats), and research animal cells (e.g. rodents). Non-limiting examples of prokaryotic cells include bacterial cells and archebacterial cells.

The cells may be derived from in vitro cultures. Suitable cell cultures may include cultures maintained by the American Type Culture Collection (ATCC), other cell depositories, or stem-cell cultures. Alternatively, the cells may be explanted from a subject before they are incubated with the nanowires. Suitable subjects include subjects in need of medical devices or implants.

Nanowires may also be used as a bioscaffold for tissue growth. Such tissue growth may be in vivo or in vitro. For instance, a bioscaffold may be used to grow tissue ex vivo for research, or for later implantion into a subject. Alternatively, a bioscaffold may be used in vivo, for example, to promote tissue regeneration. A bioscaffold may also be used in vitro to culture different tissue types. Suitable tissues may include epithelial tissue, connective tissue, muscle tissue, and nervous tissue. Epithelial tissue is typically comprised of layers of cells that cover organ surfaces, such as the surface of the skin and the inner lining of the digestive tract. Non-limiting examples of epithelial cells include squamous cells, cuboidal cells, columnar cells, and transitional cells. Epithelial cells may also be simple, stratified, or pseudostratified with cilia. Non-limiting examples of connective tissue include areolar (or loose) connective tissue (including collagen and elastin), adipose tissue, dense connective tissue (or, less commonly, fibrous connective tissue) including ligaments and tendons, reticular connective tissue (a soft skeleton to support the lymphoid organs), and specialized connective tissues. Specialized connective tissues may include blood, bone, and cartilage. In one embodiment, the nanowires may be used as a bioscaffold for growing bone tissue. Non-limiting examples of bone tissues include compact and spongy bone tissue. Muscle tissue may include smooth muscle, skeletal muscle, and cardiac muscle. Nervous tissue generally refers to tissues forming the brain, spinal cord and peripheral nervous system.

The nanowires comprising the bioscaffold may be loaded with therapeutic molecules, as described in part II(a)(ii) above. In particular, the bioscaffold may be loaded with a therapeutic agent(s) that promotes cell growth or adhesion. For instance, the nanowires may be loaded with a polypeptide or mixture of polypeptides that promotes cell adhesion and that mimics the signals that typically comprise the cell's in vivo environment. As an example, a bioscaffold may be loaded with a mixture of polypeptides and/or small molecules that promotes a stem cell's growth and differentiation into a desired tissue or organ. The types of signals that comprise a cell's in vivo environment are typically known in the art.

The bioscaffolds of the invention may be used on the surface of medical devices or implants. The bioscaffold on the medical device or implant may or may not initially comprise cells, depending on the purpose of the medical device. For instance, the bioscaffold may be "pre-seeded" with cells before implantation or use in a subject. Alternatively, the bioscaffold may only support cell growth after implantation or use in a subject. The microporous surface structure of the bioscaffold facilitates cell growth and adhesion, and thereby may aid in stabilizing the implant or device at its desired location within the subject. Alternatively, the bioscaffold on the medical device or implant may be used for drug delivery, as discussed in section (a) above. In some embodiments, the medical device or implant may comprise nanowires both as a scaffold for cell and/or tissue growth and as a drug delivery mechanism. Suitable medical devices or implants include the coated surfaces discussed in section (a)(i) above.

The bioscaffolds may be formed on materials comprising the medical device or implant prior to assembly of the medical device or implant, during the assembly or manufacture of the medical device or implant, or alternatively, after assembly. As discussed above, the bioscaffold may be loaded with therapeutic agents to promote cell attachment and/or growth and differentiation. For instance, bioscaffold surfaces may be loaded with growth factors, matrix materials, or other biological or chemical components such as Matrigel, collagen, fibronectin, laminin, poly-Lysine, or RGD containing peptides. Other extracellular matrix molecules may also be applied, including but not limited to heparan sulfate proteoglycan, keratin sulfate proteoglycan, or chondroitin sulfate proteoglycans.

The types of cells comprising the bioscaffold can and will vary depending on the use of the medical device or implant. Cells may be incubated with the bioscaffold either in vitro or in vivo (e.g. in situ). In the case of cardiovascular implants, including shunts and valves, endothelial cells or precursors of endothelial cells may be the preferred cell types. As used herein, precursor cells refer to cells capable of differentiating into the specified cell type. For instance, endothelial precursor cells are capable of differentiating into endothelial cells. In the case of bone or dental implants, osteoblasts or precursors of osteoblasts may be the preferred cell type. In the case of dermal implants, fibroblasts or precursors of fibroblasts may be the preferred cell type. In the case of cartilage implants, chondrocytes, chondroblasts, or precursors of chondrocytes may be the preferred type. Alternatively, less differentiated totipotent or pluripotent cells including embryonic stem cells or adult stem cells may be utilized. Cells may be applied to the implants either as primary isolates or established cell lines and may be derived from the subject to decrease the likelihood of subject's immune system rejecting the medical device or implant.

Non-limiting specific examples of medical devices or implant that may comprise a bioscaffold are detailed below. In each example or embodiment, the bioscaffold may also be used as a drug delivery device.

Bioscaffolds may be used to fabricate surgical implants for diseased or impaired organs, or used to grow artificial organs in vitro or in situ. The specific architecture of the implant must provide the appropriate structural integrity and support, and should be able to withstand the physical conditions of the intended organ function. A variety of scaffold types have been used in applications for wound healing and organ repair, including but not limited to, foil, mesh, tubular, fibrous, filamentous, and woven types. Non-limiting examples of organ that may benefit from a medical device or implant comprising a bioscaffold include organs of the head and neck, including the brain, skull, ears, eyes, tongue, jaw/teeth, nose, scalp, larynx, pharynx, organs of the back, including vertebra and the spinal cord, organs of the thorax, including the heart, lungs, ribs, and breasts, organs of the abdomen, including the peritoneum, the stomach, the small and large intestines, the liver, the spleen, the pancreas, and the kidneys, organs of the pelvis and perineum, including the pelvic bone, the bladder, and the uterus, and organs of the upper and lower limbs, including the associated muscles and skeletal organs, and joints such as the finger joints, the wrist, the elbow, the shoulder, the hip, the knee, the ankle, and foot joints.

Bioscaffolds of the invention may be used to promote organ-repair. Such devices may have, for example, thin flexible architecture to promote wound closure, or architecture designed to be weight bearing, useful, for instance, in bone repair. By way of example, tissue may be lost as a result of as a result of surgery or injury, thereby creating a gap or void. An implant comprising a cell-conductive support, for example, a bioscaffold of the invention, with or with out cells or therapeutic agents, may be inserted to bridge the gap and provide physical support for the organ as well as a scaffold for cell growth, thus promoting the subject's own cells to reconstruct the missing tissue. Optionally the device may be pre-seeded with cells as described above. This embodiment may be especially useful in areas of relatively high stress, such as hernia repair sites.

As discussed in part (a) above, acceptable implants include various forms of stents. A stent typically has closed cylindrical architecture, comprised of a plurality of interconnected, deformable struts arranged to provide a structure that facilitates support of a vessel or other body conduit with minimal disruption. A stent may be useful for a biological structure comprising a lumen.

The type of biological structure the stent is designed for will dictate, in part, the attributes of the bioscaffold used. Blood vessels, or other biological structures that encounter blood, for instance, typically require a stent surface that is non-thrombogenic. A stent comprising a bioscaffold may be loaded with a therapeutic agent to decrease any thrombogenic effect of the stent. Additionally, or alternatively, a bioscaffold may be used to promote adherence of endothelial cells to the stent, thereby mimicking the natural lining of blood vessels and masking possible thrombogenic effects of the stent.

Similarly, artificial heart valves may comprise a bioscaffold of the invention. Such a bioscaffold may be used to encourage tissue integration and subsequent anchorage of the device. In addition, the bioscaffold may be used to promote endothelial cell growth, thereby masking the valve from any thrombogenic effects of the device.

The invention provides a method for the production of implants or medical prostheses with tissue adherent and/or drug delivery properties for use in orthopedic applications, including devices or implants used in oral and maxillofacial surgery, and prosthetic joints. A device or implant comprising a bioscaffold may be used where tissue integration or immobilization of the device or implant is desired. Improved immobilization will decrease inflammatory reactions and the likelihood of premature implant failure. Additionally, a bioscaffold may be used to minimize calcification complications.

Bioscaffolds used in orthopedic implants may comprise therapeutic agents, such as those describe above, and may also include osteoconductive agents such as epidermal growth factor (EGF), platelet derived growth factor (PDGF), fibroblast growth factors (FGFs), parathyroid hormone related peptide (PTHrp), insulin-like growth factors (IGFs), transforming growth factor-beta (TGF-$\beta$), and bone morphogenic proteins (BMPs). Also, the orthopedic device or implant may optionally include osteoconductive materials such as calcium sulfate or calcium phosphate compounds, hydroxyapatite, deproteinized bone, or corals. Orthopedic devices or implants may be seeded with osetoblasts or osteoblast precursor cells.

Non-limiting examples of orthopedic implants that may comprise a bioscaffold include bone plates, hip nails, bone screws, femoral heads, intramedullary interlocking nails, and Kuntscher cloverleaf nails. Also included are orthopedic implants and prosthetic devices for replacement of the hip, knee, shoulder, elbow, and other joints. Additionally, orthopedic devices may be used to help promote bone growth and/or repair. Non-limiting examples of suitable bones may include the cranium, the mandible, the clavicle, the scapula, the sternum, the ribs, the vertebrae, the sacrum, the coccyx, the humerus, the ulna, the radius, the carpal bones, the metacarpal bones, the phalanges, the ilium and ischium, the femur, the patella, the tibia, the fibula, the tarsal bones, and the metatarsal bones.

For instance, a prosthetic device for hip replacement may comprise a bioscaffold. The bioscaffold may be used on the entire prosthetic device, or may be limited to points where the device interfaces with bone tissue. For example, the bioscaffold may be applied to the shaft portion of the femoral head of the implant and the external surface of the aspherical cup. Prosthetic designs for hip joints are well known in the art. See, for instance, U.S. Pat. No. 7,211,113.

Similarly bone screws, nails and the like may be treated with the process of the present invention to improve integration and biocompatibility. In one embodiment, a titanium bone implant is used to provide support for a fragmented bone. A bioscaffold on the surface of the bone plate allows for better integration of the surrounding tissue, therefore providing more secure support as well as masking the bone plate from the immune system. This may eliminate the need for removal of the screw, plate, or similar device or implant.

Dental medical devices or implants would similarly benefit from the present invention. By way of example, a jawbone implant typically comprising a screw, cylinder, or blade may comprise a bioscaffold. In particular, the device or implant may comprise a bioscaffold at the point of interface with bone or other tissue. Additionally, bioscaffolds at the interface of prosthetic teeth and the jaw would improve both integration and immobilization of the prosthetic device.

Bioscaffolds may also be applied to sutures, surgical staples, surgical grafts, screens, and patches where applicable and surface adhesion is medically appropriate. For instance, such surgical devices may be used for hernia and aortic aneurysms.

(c) Marine Antifouling Coatings

The invention also includes marine coating compositions that contain bioscaffolds comprising one or more biocides effective for preventing fouling and sliming of submersed structures by various organisms. Specifically, they are effective for preventing the attachment and propagation of organisms. For example, these organisms include barnacles (e.g., members of the class Cirripedia), tubeworms, sea mussels, Zebra mussels, hydroides, ectoprocts, tube-building amphipods, oysters, sea moss, mollusks, shellfish, ulba, enteromorpha, ectocorpus, ostrea, mytilus, ascidian, slime; seaweed and algae such as sea lettuce, green layer, marine spirogyra and red and brown bryozoan.

An underwater marine structure can be any surface that is in contact with fresh, salt, estuarine, brackish, sea or other bodies of water including, for example, ship surfaces (e.g., ship hulls, boat hulls, submarine hulls, propellers, rudders, keels, centerboards, fins, hydrofoils), deck surfaces, buoys, piers, wharves, jetties, fishing nets, cooling system surfaces, cooling water intake or discharge pipes, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pipes, pumps, valves, wires, cables, ropes, ladders, pontoons, transponders, antennae, barges, periscopes, snorkels, gun mounts, gun barrels, launch tubes, mines, torpedoes and depth charges.

Typically, marine coating compositions of the present invention include nanowire bioscaffolds comprising one or more biocides and an organic vehicle. The biocide is typically dispersed within the macropores of the bioscaffold by either covalent or non-covalent attachment in accordance with methods known in the art. Generally, the organic vehicle can be selected from a resin, a diluent and combinations thereof. Exemplary resins can be natural or synthetic resins, and can comprise solid or semisolid viscous substances that either are obtained as exudations from certain plants or are prepared by polymerization of simple molecules. Exemplary diluents are organic solvents. The marine coating compositions optionally contain additives such as pigments, fillers, swelling agents, wetting agents, biocides and combinations thereof. Suitable resins, diluents and additives are described in more detail below.

(i) Biocides

A variety of biocides are suitable for use as antifouling agents in the marine coating compositions. Non-limiting examples of antifouling agent include, for example, cuprous oxide, copper rhodanide, copper hydroxide, copper nitrate, copper (II) nitrate trihydrate, copper naphthenate, metallic copper and various tin compounds and dithiocarbamic acid derivatives, such as tetramethylthiuram monosulfide, tetramethylthiuram disulfide, zinc bis-(dimethyldithiocarbamate), zinc ethylene-bis(dithiocarbamate), manganese ethylene-bis (dithiocarbamate), and copper bis(dimethyldithiocarbamate) and combinations thereof. Non-limiting examples of organometallic biocides include zinc pyrithione, ZINEB, and copper naphthenate. Non-limiting examples of organic biocides include IRGAROL 1051 or SEANINE211

(ii) Organic Vehicles

The marine coatings and marine coating compositions of the present invention comprise an organic vehicle. The organic vehicle is selected from the group consisting of resins, organic diluents and combinations thereof. Various preferred embodiments of the marine coatings contain a resin. In preferred embodiments of marine coating compositions, the organic vehicle comprises a resin and a diluent. Suitable resins and diluents are discussed in more detail below.

In one embodiment the organic vehicle may be a self-polishing co-polymer. Exemplary self-polishing copolymers are acrylic resins (e.g., polyester acrylic resins, epoxy acrylic resins, polyether acrylic resins, vinyl acrylic resins, styrene/acrylic copolymer resins, urethane acrylic resins, fluoroalkyl (meth)acrylate/silyl (meth)acrylate/alkyl (meth)acrylate terpolymers (e.g., as described in U.S. Pat. No. 6,767,978, expressly incorporated herein by reference) acrylic emulsion resins and polyol acrylic resins), copolymers of vinyl chloride, vinyl isobutyl ether, carboxylic acid functional polymers and combinations thereof.

In another embodiment the organic vehicle may be an ablative coating. Ablative coatings contain resins that are soluble in water to the extent that the coating is gradually washed away through contact of the coated structure with water. The rate at which the coating is dissolved is controlled and depends on the solubility of the resin. Exemplary ablative resins are selected from the group consisting of vinyl resins, alkyd resins, epoxy resins, acrylic resins, polyurethane resins, polyester resins, vinyl acrylic resins, vinyl esters (e.g., vinyl esters of $C_{2-20}$ linear or branched alkanoic, alkenoic, alkyldienoic acids) and combinations thereof.

The resins of the organic vehicle may also comprise rosins. For example, suitable rosins are selected from the group consisting of gum rosin, wood rosin of grades B, C, D, E, F, FF, G, H, I, J, K, L, M, N, W-G, W-W (as defined by the ASTM D509 standard), virgin rosin, hard rosin, yellow dip rosin, NF wood rosin, tail oil rosin, colophony, colophonium, single constituents of natural rosin (e.g., abietic acid, abietinic acid, sylvic acid, dihydroabietic acid, tetrahydroabietic acid, dehydroabietic acid, neoabietic acid, pimaric acid, laevopimaric acid, isopimaric acid, sandaracopimaric acid, palustric acid, dextro-pimaric acid, isodextro-pimaric acid, dextro-pimarinal, isodextro-pimarinal, xanthoperol, tatarol, podocarpic acid, phyllocladen, sugiol, ferruginol, himokiol, manool, manoyloxide, ketomanoyloxide, cativinic acid, eperuanic acid and all other rosin components based on the diterpene skeleton of abietic acid) and combinations thereof.

The marine coating compositions of the present invention are usually formulated and used in the form of paint compositions. But they may be formulated and used in other forms (such as solutions or emulsifiable concentrates) as the case requires. Paint vehicles to be used for formulating the compounds of the present invention into coating compositions, may include other resins in additional to those described above. For example, a vinyl chloride resin, a vinyl chloride-vinyl acetate copolymer, a vinyl chloride-vinyl isobutyl ether copolymer, a chlorinated rubber resin, a chlorinated polyethylene resin, a chlorinated polypropylene resin, an acrylic resin, a styrene-butadiene resin, a polyester resin, an epoxy resin, a phenol resin, a synthetic rubber, a silicone rubber, a silicone resin, a petroleum resin, an oil and fat resin, a rosin ester resin, a rosin soap or rosin may be used.

(iii) Diluents

In various embodiments, the marine coating compositions also contain a diluent. The diluent is selected from the group consisting of alcohols, aliphatic, cycloaliphatic and aromatic hydrocarbons, ketones, ether alcohols, esters, chlorinated hydrocarbons and combinations thereof. Typically, the diluent may function as a solvent for the antifouling agent and/or for a resin component of the composition. Preferably, the diluent is selected from the group consisting of methanol, ethanol, propanol, isopropanol, butanol, isobutanol, benzyl alcohol, white spirit, cyclohexane, toluene, xylene, methyl ethyl ketone, acetone, methyl isobutyl ketone, methyl isoamyl ketone, diacetone alcohol, cyclo-hexanone, 2-butoxyethanol, propylene glycol monomethyl ether, butyl diglycol, methoxypropyl acetate, n-butyl acetate, 2-ethoxyethyl acetate, methylene chloride, tetrachloroethane, trichloroethylene and combinations thereof.

In the marine coatings of the present invention, typically, the diluent evaporates once the coating composition is applied to the marine structure. Therefore, the dried and/or cured marine coatings have a minimal concentration of diluents in the coating.

(iv) Additives

In general, additives may be contained in the marine coating compositions and marine coatings. Additives may be selected from the group consisting of pigments, fillers, extenders, swelling agents, wetting agents, biocides and combinations thereof. Pigments, for example, can be organic or inorganic pigments. Typical pigments for use in marine coatings are selected from the group consisting of phthalo blue, hansa yellow, ochres, umbers, Quinacridone Red, Pigment Red, Phthalocyanine Blue, Phthalocyanine Green, Perylene Red, carbon black, rutile and anatase titanium dioxides, lithopone, zinc sulfide, lead titanate, antimony oxide, zirconium oxide, barium sulfide, white lead, zinc oxide, leaded zinc oxide, red iron oxide, brown oxide, aluminium powder, vapor-deposited aluminium powder, alumina powder, nickel powder, copper powder, brass powder, chromium powder, nacreous pearl mica powder and nacreous colored pearl mica powder and combinations thereof.

Fillers are materials that usually have a fine particle size, are dispersable in organic media and do not settle once dispersed. Exemplary fillers are selected from the group consisting of calcium carbonate, iron oxide, kaolin, clay, titanium dioxide, alumina trihydrate, pyrophyllite, quartz, silica, fumed silicas, precipitated silicas, silicates, barium sulfate, antimony oxide, mica, calcium sulfate, magnesium hydroxide, feldspar, nepheline syenite, carbon black filler, titanates, talc, gypsum, silex, wollastonite, bagasse, coconut hull/fiber, cork, corn, cotton-based, filsonite, nutshell flour, rice hull, sisal/hemp, soybean, starch wood flour and combinations thereof.

Swelling agents are compounds that increase in volume when in contact with a liquid. Preferably, swelling agents are included in the ablative marine coating compositions because the presence of the swelling agent aids the coating degradation by helping the coating to "slough off" upon contact with water. Suitable swelling agents are selected from the group consisting of modified bentonite, kaoline, montomorillonite bentonite, clay mica (muscovite), cholorite (hectonite), non-alkaline magnesia alumosilicate, quartz, silica, high silica, soda silicate, magnesia alumosilicate, soda borosilicate, polycarbonsilane, polytitanocarbosilane, polysilazane, tobermorite, samarium silicate, wollastonite, potassium aluminium silicate, hydroxyapatite, calcium hydrogenphosphate, neodymium pentaphosphate, silver phosphate, calcium sulfate, calcium iodate, phlogopite, biotite, sodium aluminium hydroxycarbonate, rockwool, basalt rockwool, processed mineral fibers, volcanic rock, atapulgite, calcined bauxite and combinations thereof. In preferred embodiments, the marine coating and the dried and/or cured marine coating composition comprise a modified bentonite available from NL Chemicals under the trade name Bentone SD®.

Wetting agents are substances that reduce the surface tension of a liquid and cause the liquid to spread across or penetrate more easily the surface of a solid. Exemplary wetting agents are selected from the group consisting of a solution of a salt of unsaturated polyamine amides and lower molecular acid polymers, sodium polyphosphate, aryl or alkyl phosphates, salts of low molecular weight poly (acrylic acid), salts of sulfonated polyethylene, salts of poly (vinylphosphonic acid), salts of poly (maleic acid), salts of copolymers of maleic acid with olefins, and combinations thereof. In preferred embodiments, the dried and/or cured marine coating and the marine coating composition comprise a solution of a salt of unsaturated polyamine amides and lower molecular acid polymers sold by BYK Chemie under the trade name Anti-Terra®-U.

Representative non-limiting formulations for ablative and self-polishing copolymer (SPC) marine coating compositions are presented in Table 1 below.

TABLE 1

Marine paint compositions

| | Material | PERCENT |
|---|---|---|
| Ablative | | |
| CU | | |
| Acros Organics | Cuprous Oxide | 35.0-45.0 |
| Aldrich | Zinc Oxide | 8.0-15.0 |
| Bayer | Iron oxide (filler) | 1.5-3.0 |
| NL Chemicals | Bentone ® SD | 0.5-1.2 |
| Rohm & Haas | Metamare ® B175 | 18.0-25.0 |
| Byk Chemie | Antitera ® -U | 0.5-01.5 |
| Aldrich | Mixed Solvent | 20-3 |
| Metal Free | | |
| Aldrich | Cuprous Oxide | 0.00 |
| | Zinc Oxide | 35.0-50.0 |
| NL Chemicals | Bentone ® SD | 0.5-2.0 |
| Rohm & Haas | Metamare ® B175 | 20.0-35.0 |
| Byk Chemie | Antitera ® -U | 0.4-0.9 |
| Aldrich | Mixed Solvent | 30.0-45.0 |

TABLE 1-continued

Marine paint compositions

| | Material | PERCENT |
|---|---|---|
| SPC Type | | |
| copper | | |
| Brand NU Labs | Cuprous Oxide | 35.0-45.0 |
| Aldrich | Zinc Oxide | 8.0-12.5 |
| Bayer | Iron oxide (filler) | 2.5-5.0 |
| Aldrich | Rosin | 8.0-15.0 |
| | Acrylic Resin | 5.0-10.0 |
| BASF | Ext. Resin (Laroflex ® type) | 3.0-6.0 |
| Aldrich | Mixed Solvent | 20.0-30.0 |
| Metal Free | | |
| Aldrich | Cuprous Oxide | 0.00 |
| | Zinc Oxide | 1.0-3.5 |
| Bayer | Iron oxide (filler) | 15.0-28.0 |
| Aldrich | Rosin | 5.0-15.0 |
| | Acrylic Resin | 5.0-15.0 |
| BASF | Ext. Resin (Laroflex ® type) | 3.0-8.0 |
| Aldrich | Mixed Solvent | 40.0-50.0 |

(d) Airplane Coating

Yet another use for the nanowire scaffolds formed by the process of the invention may be a surface coating for an aircraft or an aerospace vehicle. The coating may interact, through absorption or reflection, with specific regions of the electromagnetic energy spectrum. The regions of interest in the electromagnetic energy spectrum include the ultraviolet, visible, infrared, or microwave (such as radar) regions. The coating may be used to shield the electronic control and communication systems from electromagnetic interferences, such as lightening strikes, interference from radio emitters, nuclear electromagnetic pulses, or high power microwave threats. Furthermore, the coating may be used for radar avoidance. Additionally, the coating may also protect the vehicle from environmental conditions, such as moisture, temperature changes, and pollution. Such environmental exposure may corrode the airframe, skin and other bonded joints, thereby damaging the conductivity and electromagnetic shielding of the vehicle. In yet another embodiment, the coating may enhance the aerodynamics of the vehicle, thereby reducing friction, turbulence, and noise, and/or enhancing control of the vehicle.

The coating may comprise the nanowire scaffolds. In one embodiment, the nanowire scaffolds may comprise aluminum. In an exemplary embodiment, the nanowire scaffolds may comprise titanium. In still another embodiment, the nanowire scaffolds may further comprise a near infrared absorbing material, such as aminium and diimmunoium salts. In another alternate embodiment, the nanowire scaffolds may further comprise an infrared or radar absorbing material, such as spinel ferrite. In yet another embodiment, the nanowire scaffolds may further comprise a chromophore capable of absorbing electromagnetic radiation having a wavelength of greater than about 0.7 micron.

(e) High Temperature Catalysis

The nanowire scaffolds formed by the process of the invention may also be used as a support for catalysts utilized in high temperature reactions. In general, high-temperature catalysis is defined as occurring at temperatures between 400° C. to 1200° C. Examples of suitable reactions falling into this category include the oxidation and the oxidative dehydrogenation of light alkanes to oxygenates and olefins; the catalytic partial oxidation of methane and higher hydrocarbons to syngas, e.g. for fuel-cell applications; the oxidation of ammonia to nitrogen(II) oxide; the production of hydrogen cyanide by the conversion of ammonia with methane; automotive exhaust catalysis; and catalytic combustion. For example, the nanowire scaffolds may be utilized as a catalyst support for catalytic cracking, which is the process whereby complex organic molecules such as kerogens or heavy hydrocarbons are broken down into simpler molecules (i.e., light hydrocarbons such as LPG, gasoline, light cycle oils used in diesel and jet fuels, and heavy fuel oil) by the breaking of carbon-carbon and/or carbon-hydrogen bonds in the precursors. Typically, the precursors are heated from about 500° C. to about 800° C. in the presence of a solid acid catalyst (e.g., aluminum oxide, silicon dioxide) or a zeolite-based catalyst. Typically, the spent catalyst is separated from the reactants, stripped of deposited hydrocarbons, and regenerated by exposure to air (or oxygen) to burn off the accumulated coke and restore catalyst activity. Having the catalyst supported on a solid matrix comprising a nanowire scaffolds may facilitate and expedite these processes, thereby decreasing the costs associated with the petroleum cracking process.

Thus, the present invention can find many applications in a wide spectrum of fields, such as:

(1). A marine coating composition, the composition comprising an organic vehicle and the nanowire scaffold provided by this invention, the nanowire scaffold comprising an antifouling agent, wherein the antifouling agent inhibits fouling by an organism selected from the group consisting of barnacles, Balanus amphitrite Darwin, Zebra mussels, tubeworms, oysters, algae, bacteria, and a biofilm.

(2). A method for inhibiting fouling of a marine structure, the method comprising applying the marine coating composition of (1) to the marine structure. The marine structure is selected from the group consisting of ship hulls, boat hulls, submarine hulls, propellers, rudders, keels, centerboards, fins, hydrofoils, deck surfaces, buoys, piers, wharves, jetties, fishing nets, cooling system surfaces, cooling water intake or discharge pipes, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pumps, valves, wires, cables, ropes, ladders, pontoons, transponders, antennae, barges, periscopes, snorkels, fun mounts, gun barrels, launch tubes, mines, torpedoes and depth charges.

(3). A method for delivery of a therapeutic molecule to a subject, the method comprising: (a) coating a biocompatible surface with the nanowire scaffold provided by this invention, the nanowire scaffold comprising a therapeutic molecule; and (b) contacting the coated biocompatible surface with the subject in a manner such that the therapeutic molecule is released from the surface. The coated biocompatible surface is contacted with a part of the subjected selected from the group consisting of a cell, tissue, vessel, artery, and organ. The biocompatible surface is selected from the group consisting of bones, joints, and medical devices. The medical device can be, for example, a stent or valve or the like. The therapeutic molecule is released from the biocompatible surface in a time controlled manner.

(4). A biocompatible surface coated with a nanowire scaffold provided by this invention, the nanowire scaffold comprising a therapeutic molecule.

(5). A bioscaffold comprising the nanowire scaffold provided by this invention, the nanowire scaffold comprising a plurality of growing cells. The bioscaffold further comprises a therapeutic agent. The cells are osteoblasts or osteoblast precursor cells, wherein the cells comprise tissue selected from the group consisting of endothelial tissue, connective tissue, muscle tissue and nervous tissue.

(6). A method for growing cells, the method comprising (a) contacting a cell with a nanowire scaffold provided by this invention, and (b) incubating the cells under conditions that promote cell growth.

(7). A medical device or implant comprising a bioscaffold provided by this invention. The medical device or implant can be an orthopedic medical device or implant selected from the group consisting of bone plates, screws, nails, and prosthetic joints. The medical device or implant can also be a stent or valve or the like.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The following examples are included to illustrate exemplary iterations of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

Materials and Methods for Examples 1-4

Preparation of the Nanofiber Scaffolds

Titanium foil (Alfa Aesar, Ward Hill, Mass.) was washed in 10 mL acetone solution at room temperature (22-24° C.), rinsed with deionized water, and transferred into a Teflon-lined vessel containing 10 mL NaOH (0.20 mol/L to 10.0 mol/L) solution and P-25 (0-0.1 g). The container was thereafter sealed and placed in the oven (VWR, mode 1350FM). After a hydrothermal treatment at 150-250° C. for 1-10 hours, the nanofiber scaffolds were formed on the metal. The product was collected, washed with deionized water to a pH value of 7.0, and air-dried.

Scanning Electron Microscopy and X-Ray Diffraction:

Scanning electron microscopy (SEM), transmission electron microscopy (TEM), and x-ray diffraction (XRD) studies were carried out to characterize the bioscaffolds formed from the hydrothermal syntheses. Morphologies of the resulting material were mainly examined under SEM (Hitachi S2300). The TEM image was collected on a JEOL X-100 microscope and the XRD data from the Philips X'Pert X-ray Diffractometer.

Cell Culture:

To investigate the applicability of bioscaffolds in the growth of tissues or cells in vitro, scaffolds grown on titanium plates were sterilized in 70% ethanol v/v at room temperature, rinsed in sterile 0.9% saline w/v, and placed into culture plates. Subsequently, mesenchymal stem cells, prepared and transduced with green fluorescent protein for visualization based on the literature method [1], were suspended in DMEM-LG medium (Gibco, Grand Island, N.Y.) supplemented with 10% fetal bovine serum (Hiclone, Logan, Utah), and added to the culture plates and allowed to adhere for 48 hours. Images of cells on the scaffolds were acquired using an Olympus fluorescent microscope.

Controlled Release:

A piece of dried titanium foil (2.2 $cm^2$) that was coated with nanofiber scaffolds was soaked in 100 mL of 0.001 mol/L crystal violet ($C_{25}H_{30}ClN_3$, as a simulated drug) solution for 12 hours at room temperature. Then, the foil was collected, rinsed with deionized water, dried at room temperature overnight, and placed in 10 mL of fresh water for releasing the crystal violet molecules. The released crystal violet was measured on the Beckman DU-530 UV-Visible Spectrometer.

Example 1

X-Ray Diffraction (XRD) Patterns

The plot in FIG. 1A is a typical x-ray diffraction (XRD) pattern of the pure Ti foil. FIG. 1B shows clear diffraction peaks of the titanate on the Ti foil, suggesting that the scaffolds are formed by the titanate nanowires [2,3]. It was observed in our work that after being calcined at 400° C., the scaffolding NWs were transformed to the $TiO_2$—B phase (a=12.1787, b=3.7412, c=6.5249, $\beta$=107.0548), and then the $TiO_2$—B can change to the anatase structure at 800° C. (data not shown). Such a series of structural transformations at elevated temperatures agrees well with the results reported by others in the literature [4-6].

Example 2

Scanning Electron Microscope Studies of Nanofibers

Figure 2:
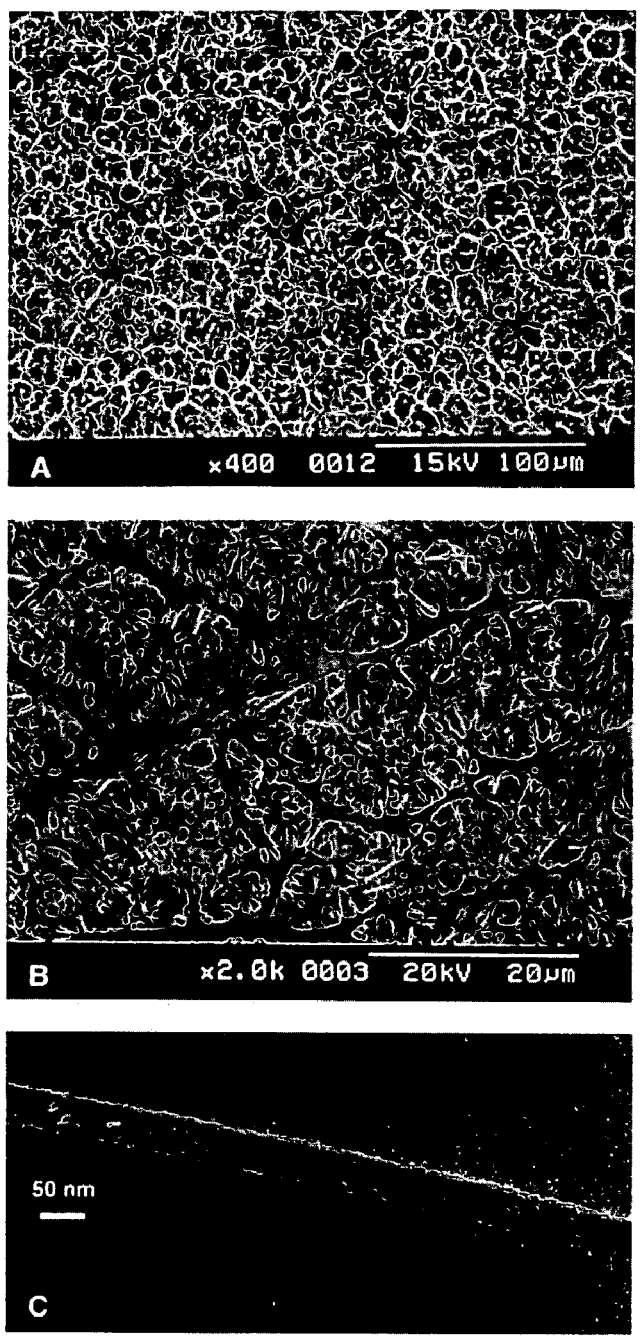
FIG. 2 depicts scanning electron microscopy (SEM) and transmission electron microscopy (TEM) images of the nanofibers. (a) Low-magnification and (b) high-magnification SEM photographs of the 3D nanofibers scaffolds on the foil. (c) TEM image of a typical nanofiber.
Figure 3:
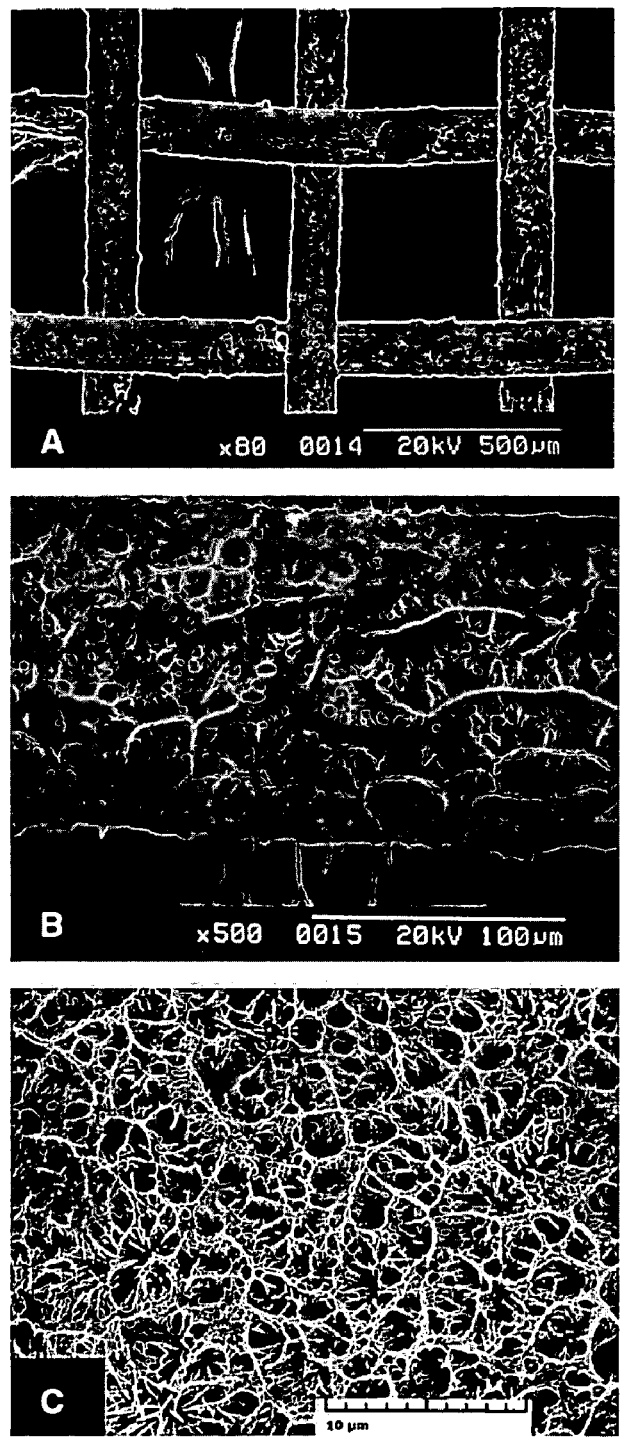
FIG. 3 depicts SEM image of arrayed nanofibers on the Ti mesh. (A) A low magnification SEM photograph of Ti mesh coated with the nanowires. (B) and (C) High-magnification SEM photograph showing the 3D porous nanofibers on the Ti mesh.

FIG. 2 demonstrates the SEM photomicrographs of the $TiO_2$ nanofiber scaffolds on the Ti. FIG. 2a provides a low-magnification survey photograph for showing (i) uniformity and (ii) purity of the nanofibers-based scaffolds over the entire surface of the Ti foil.

At the high magnification, the SEM photographs from a tilted sample reveal details about the nanofibers self-organization into the 3D scaffolds (FIG. 2b). These nanofibers have the length controllable from 5 to 20 μm. FIG. 2c shows a TEM image of a typical nanofiber with the average diameter of about 60 nm.

Example 3

Scanning Electron Microscope Studies of Nanofibers on TI Mesh

For studying whether macroporous scaffolds could be coated on Ti mesh surface [7], a similar synthesis on Ti mesh surface is successfully performed. FIG. 3A depicts an SEM photograph of the scaffold coating on the Ti mesh. A high-resolution SEM photograph (FIGS. 3B and 3C) from the same sample reveals that the nanofibers have self-organized into the 3D scaffolds, very much like that formed on the Ti foil (see FIG. 2b). It is expected that such NW scaffolds on the Ti mesh can be a potentially good biomaterial candidate for regeneration of hard tissues, because the tissue may be able to grow not only into the macroporous bioscaffolds but also the nearly millimeter-level mesh voids.

Example 4

Growths of Cell Colonies on the Nanowire Bioscaffolds

The development of a new coating good for cell/tissue growths has been one of the main focuses in modern tissue engineering. Titanium is a common biomaterial widely used in biomedical implantation because of its superb biocompatibility, toughness, and strength-to-weight ratio, which for decades has motivated many researchers to work on modifications of the Ti metal surface. Recently, colonization of preosteoblastic cells on organoapatite-titanium mesh was conducted by Stupp's group [7]. These results suggest that the organoapatite coating on the Ti mesh wire is capable of inducing accelerated colonization of unseeded implant structures by osteogenic cells [8].

An ideal bioscaffold would normally possess good biocompatibility, ample void space inside interconnected macropores, and sufficient mechanical strength [9]. The titanate nanofiber scaffolds developed herein were found to be able to provide a proper environment for the formation of the cell colonies in a dense array. As compared with the literature results, our NW bioscaffolds on Ti mesh would outperform in cell/tissue regeneration.

Figure 4:
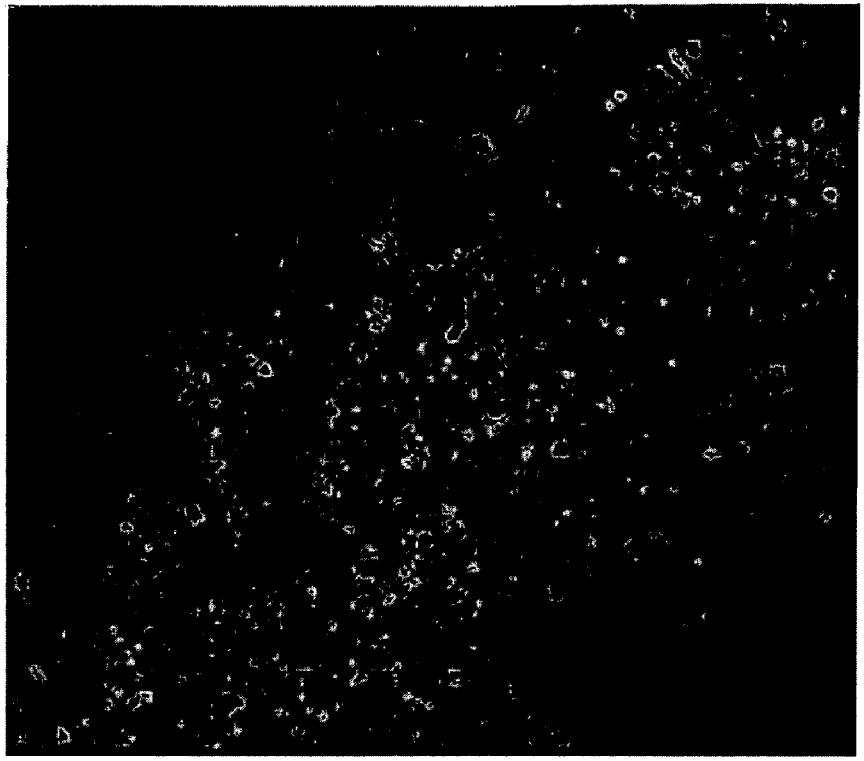
FIG. 4 depicts micrographs of the growth of stem cells on the nanowire scaffold after 2 days.
Figure 5:
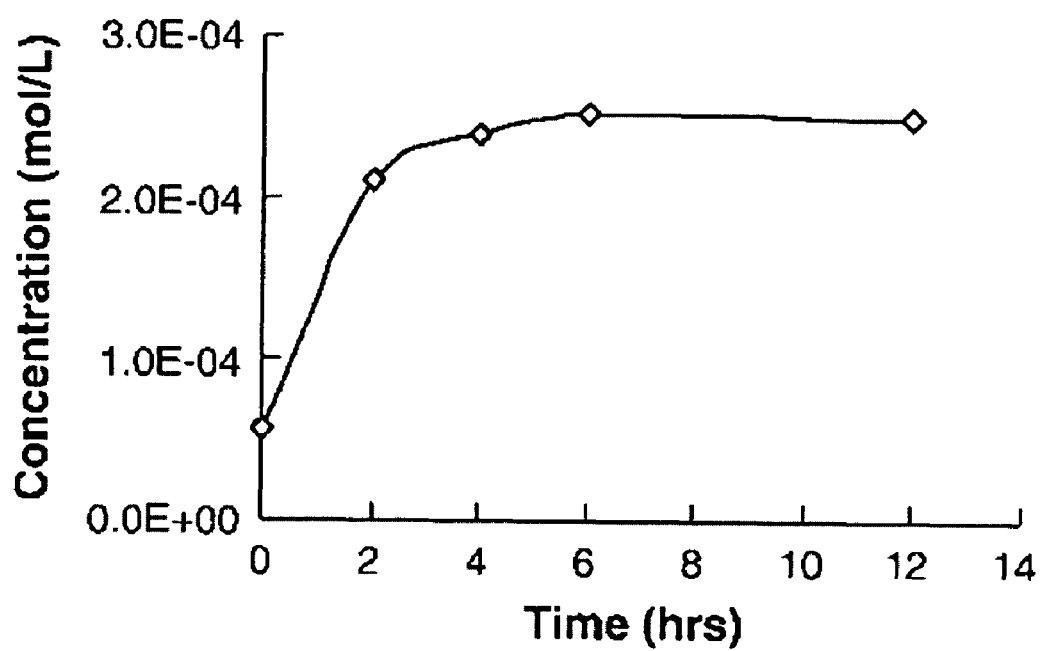
FIG. 5 depicts a graph showing the controlled drug release within 12 hours using the Ti foil coated with the nanofiber scaffold expressed as moles per liter.

For cell growth, mesenchymal stem cells were used to evaluate the compatibility of the scaffolding nanofibers. One day after the cells were introduced onto the scaffold, the cells adhered well onto the nanofiber scaffold. After 2 days new cells could be clearly seen on the nanofiber scaffolds. FIG. 4 shows a fluorescence microscopy photo image of the dense array of cell colonies on the scaffold and populated densely across the entire substrate that is the Ti foil. This implies that the nanofiber scaffolds as such may potentially serve as a biocompatible macroporous scaffold for tissue regeneration. It is believed that the highly scaffolding nanofibers may provide the dense population of cellular binding sites and the ample space for tissue cells to grow into, which is one of the major criteria for realizing the enhanced cellular activities [10].

Materials and Methods for Examples 5-8

Preparation of Self-Assembled Titanate Nanowires

Titanium substrates (foil and mesh from Alfa Aesar, and Ti-TEM grids from Ted Pella) were inserted in 10 mL acetone at room temperature, sonicated for 10 minutes, and rinsed with deionized water thereafter. The Ti substrates were then placed in a Teflon-lined vessel containing 10 mL of 1.0 mol/L NaOH solution, and then hydrothermally heated at 180-250° C. for 2-10 hours. Thus-treated Ti substrates, covered by the tough scaffolds of the titanate nanowires, were finally rinsed with deionized water and dried in air.

Characterizations:

The phase purity and crystalline structure of the nanowires were characterized by X-ray diffraction (XRD) on a Philips X'Pert X-ray diffractometer (Cu K$\alpha$, $\lambda$=1.5418 Å) scanning from 4° to 70° (2θ) at a speed of 1°/min. The morphology of the nanowire scaffolds was examined under an optical microscope (Olympus BX 51), a scanning electron microscope (SEM, Philips SEM XL30), and a high-resolution transmission electron microscope (HRTEM, JEOL 2010) performed at 200 keV.

Supported Growths of Tissues from Mesenchymal Stem Cells and Osteoblasts:

The scaffolds on titanium were first sterilized in 70% ethanol, rinsed in sterile 0.9% saline, and put into culture plates. Subsequently, mesenchymal stem cells were prepared and transduced with GFP for visualization [1], then suspended in DMEM-LG media (Gibco, Grand Island, N.Y.) containing 10% fetal bovine serum (Hiclone, Logan, Utah), added to the culture plates, and allowed to adhere for 24 hours. Another media, containing 10 mM sodium β-glycerophosphate, 100 nM dexamethasone, and 50 nM ascorbate (Sigma, St. Louis, Mo.), was used to promote the osteoblast differentiation. For in vivo testing, the scaffold-coated Ti meshes were implanted into SCID mice after the adherence of cells, and removed 4 weeks after the implantation. The in vitro samples were characterized using a fluorescent microscope, and the in vivo samples were examined under the low vacuum SEM operation mode (Philips SEM XL30). X-Ray radiographs were taken with the AXR Minishot 100 beryllium source (Associated X-Ray Imaging Corp., Haverhill, Mass.) with a 20-second exposure at 42 kV. All the studies and procedures were approved by the Institutional IRB and the animal care and use committee.

Controlled Release:

A piece of dried titanium foil (2.2 cm$^2$) pre-coated with the nanowire scaffolds was soaked in 100 mL of 0.001 mol/L crystal violet ($C_{25}H_{30}ClN_3$, as a simulated drug) solution for 12 hrs at room temperature. Then, the foil was collected, rinsed with deionized water, dried at room temperature overnight, and was then placed in 10 mL of fresh water for releasing the crystal violet molecules. The released crystal violet was measured on the Beckman DU-530 UV-Visible Spectrometer.

Example 5

Figure 6:
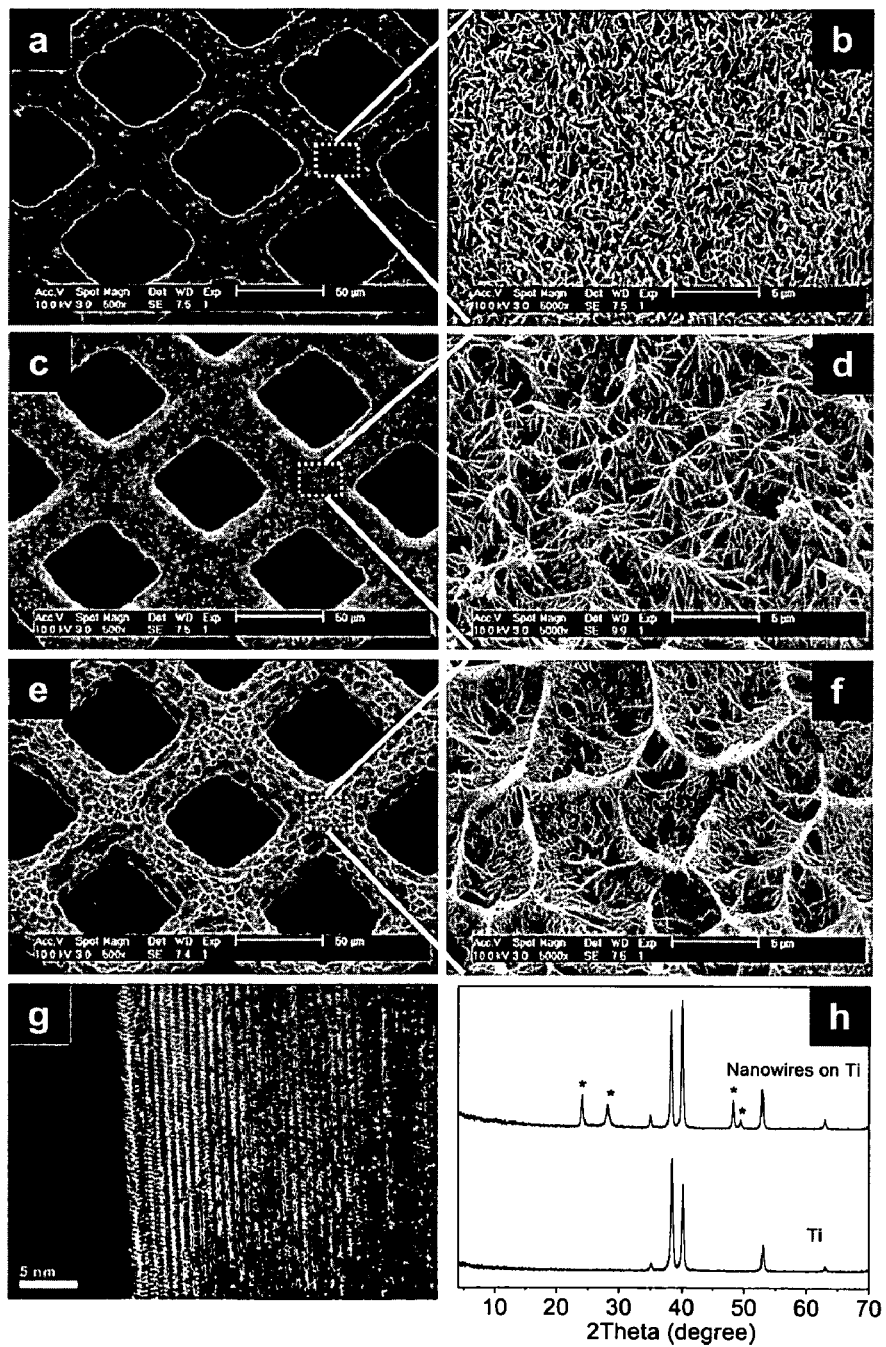
FIG. 6 depicts SEM images of nanowires formed on Ti mesh after being oxidized in various 10 ml NaOH solutions at 240° C. for 4 hrs. (a-b) 0.25 mol/L NaOH, (c-d) 0.5 mol/L NaOH, (e-f) 1.0 mol/L NaOH, (g) a high-resolution transmission electron microscopy (HRTEM) image showing the layered titanate lattice. (h) XRD patterns of the Ti and the nanowire-on-Ti.
Figure 7:
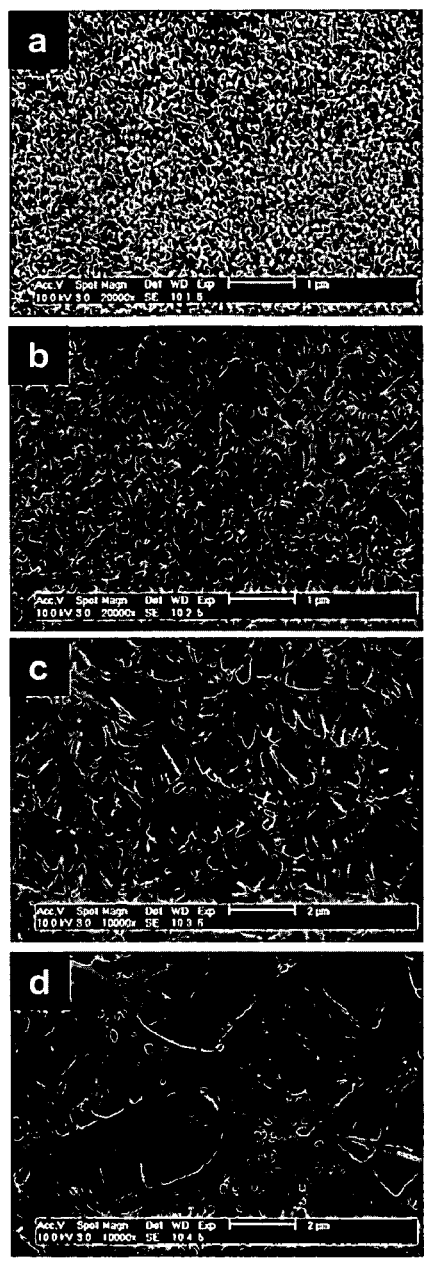
FIG. 7 depicts an SEM study of nanowire self-assembly on Ti over time. (a) 0.5 hr, (b) 1 hr, (c) 2 hrs, and (c) 4 hrs. All were formed at 240° C. in a 1.0 mol/L NaOH solution.
Figure 8:
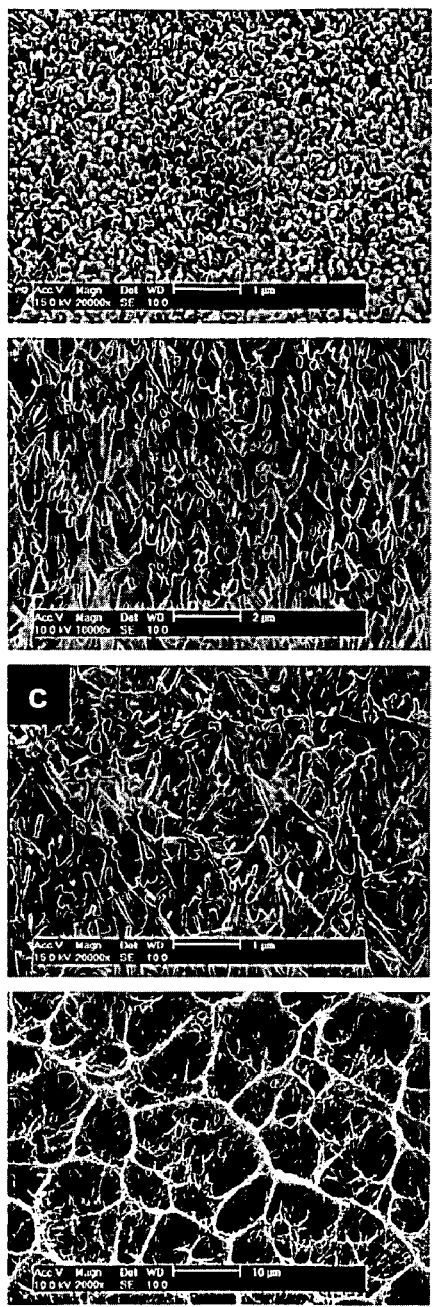
FIG. 8 depicts SEM study on the evolution of nanowire self-assembly at different temperatures. (a) 210° C., (b) 220° C., (c) 230° C., and (d) 240° C. All were formed in a 1.0 mol/L NaOH solution after 4 hrs on the Ti substrate.

Effects of Kinetic Parameters on the Growth and Self-Assembly of the Nanowire Scaffolds The new NW structural evolution and self-assembly on Ti, from a 4-hour treatment in NaOH solutions at 240° C. rather than at 180° C. [14], were studied under the SEM (FIG. 6). FIG. 6a shows a low magnification SEM picture of oriented titanate nanorods grown in a 0.25 mol/L NaOH solution, with the diameter of <200 nm and length of ~2 μm (FIG. 6b). When the NaOH concentration was increased to 0.50 mol/L, the oriented NWs, about 80 nm wide and 5 μm long, formed and started to self-assemble on Ti (FIG. 6, c-d. From the 1.0 mol/L NaOH, however, much longer NWs, nearly 50-100 nm in width and 5-10 μm in length, grew on Ti and self-assembled into macroporous scaffolds (FIG. 6, e-f). This alkali concentration effect would reflect a NW growth kinetics determined likely by the supersaturation degree [15] of the nanowire structural building blocks brought into solution by NaOH dissolution. A high-resolution transmission electron microscope (HRTEM) image of a typical NW (FIG. 6g) is similar to that of titanate. The X-ray diffraction (XRD) pattern (FIG. 6h) of the NWs resembled that of layered titanate structure [16]. Evidently, the tunable interlayer distance depending mainly on the size and hydration degree of the counter-cation (e.g. Na$^+$) [17] in the interlayer space may contribute to the mechanical flexibility or the toughness of such NWs [18].

A time study was conducted for understanding the self-assembly seldom-reported in nanosynthesis. After a hydrothermal reaction for 30 min at 240° C. in a 1.0 mol/L NaOH solution, dense and oriented nanorods (about 50-100 nm wide and 200 nm long, see FIG. 7a) have grown on the Ti. After 60 min, the nanorods became 400 nm long and bent atop (FIG. 7b). A longer reaction time (e.g. 2 hrs) would result in longer NWs, 50-100 nm in width and 2-5 µm in length, self-assembling into the scaffold (FIG. 7c) rather than further growing vertically and randomly. After a four-hour reaction, the NWs self-assembled atop into bundles. The bundles first formed "ridges" that in turn formed "valleys" about 2-10 µm in diameter and 2-5 µm in depth on Ti (FIG. 7d). Evidently, the bent NWs on the "ridge" slope implies such a self-assembly history that the tall NWs' bent tips may first slowly "swirl" around in solution, and then bind together at their tips to form the bundles that further grow to form the "ridges" and in turn the "valley". This new hierarchical self-assembly across several length scales may be governed by the surface tension [19], or static charge [20], or even H-bonding between surface hydroxyl groups on the adjacent NWs.

The temperature-dependent study was synthetically conducted for further understanding the morphology evolution in this nanosynthesis. The hydrothermal reactions were completed in a 1.0 mol/L NaOH solution for 4 hrs at different temperature. At 210° C., about 50-100 nm wide and 200 nm long oriented nanorods have grown on the Ti (FIG. 8a). Increasing the temperature to 220° C. will cause the average height of the nanowires to extend to 1-2 µm (FIG. 8b). A higher reaction time (230° C.) would result in longer NWs that bent atop and then self-assembled into bundles, with 50-100 nm in width and 2-5 µm in length (FIG. 8c). After a four-hour reaction at 240° C., the NWs hierarchically self-assembled into 3D macroporous scaffolds, with caves that are 2-µm in diameter and 2-5 µm in depth (FIG. 8d).

Example 6

Bi-Directional Co-Growth of the Organized Nanowires

Coated scaffold on Ti is resistant to nail scratches, which is different from most nanostructured coatings done in solution and implies an unusual resistance to wearing and abrasion. For understanding this property, another SEM study was conducted on a 45°-cross-section sample, and three interesting sections (FIG. 9a) were found. The top region 902a, 902e is full of organized titanate NW scaffolds, and the bottom region 906a, 906e is the metallic Ti. The middle portion 904a, 904e, however, is a corrosion region composed of mostly titanate nanoparticles (NPs) together with some NWs vertically rooted on the NPs (FIG. 9, b-c) [21,22], disclosing a continuous process of a possible NP-to-NW downward growth. This mechanism is not before known. The corrosion part is about 4 µm thick after 30 min, 10 µm thick after 2 hrs, and 20 µm thick after 4 hrs of the reaction, forming a tough and thick base for the NWs to root deeply inside (FIG. 9d) and grow downward. Only with the downward growth could the NW keep a nearly vertical orientation at its root all the time. If without the downward growth, the scaffold may quickly become free-standing due to the continuous dissolution of the NPs by the alkali in solution [32], which is not the case here and in turn explains why the NW-scaffold coating on Ti is so robust. The shape and size of the "valleys" in FIG. 6f are greatly different from those in FIG. 7d and FIG. 8d, showing that the scaffold structure is tunable over a wide range for fitting different needs in applications. In addition, the NWs are stable in strong acids (e.g. HCl) and bases (e.g. KOH) due to the chemical inertness of the titanate.

Further, a second growth for 4 hrs at 140° C. was applied to the NWs, because the multi-walled nanotubes preferably formed below 150° C. [14,23] could be easily identified. After the second growth, typical open-ended nanotubes can be seen at the NW tip (FIG. 9d), with an outer diameter about 80 nm and inner diameter 50 nm, confirming a solution upward growth at the NW tip. With the self-explanatory mechanism of the self-assembly omitted for clarity, the new upward and downward co-growth in to region 902e and middle region 904e is schematically shown in FIG. 9e.

Example 7

Effective Growths of Tissues from Mesenchymal Stem Cells and Osteoblasts

Figure 10:
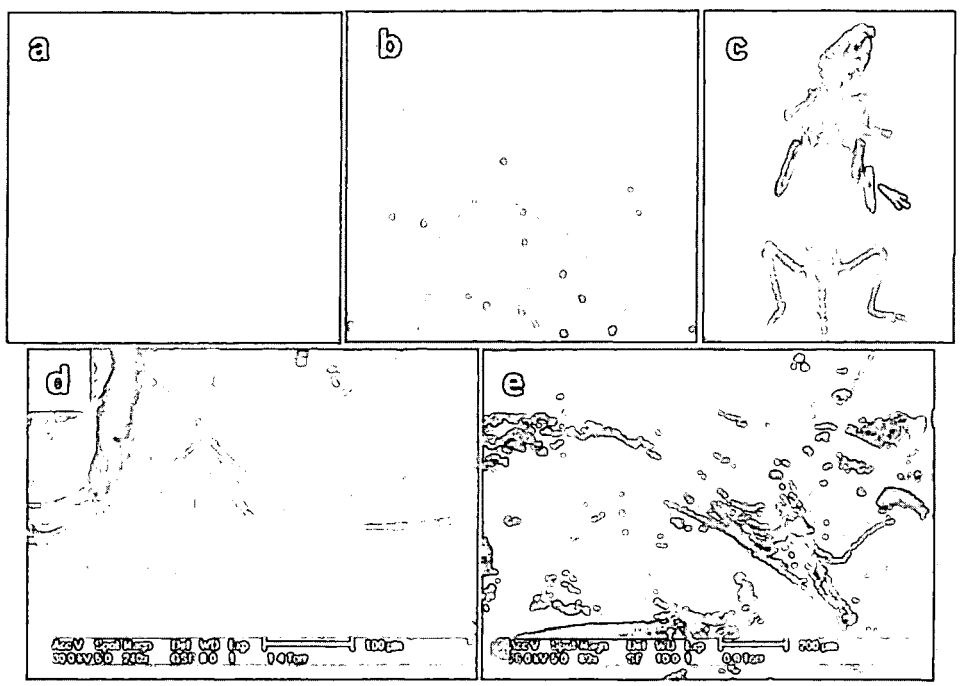
FIG. 10 depicts micrographs of tissues formed on the nanowire scaffold pre-fabricated on Ti. (a) Fluorescent micrograph of stem cells after one day on the nanowire scaffold. (b) A fluorescent micrograph of the tissues formed after 42 days from an in vitro growth. (c), An X-Ray radiograph of the bioscaffolds 4 weeks after being implanted inside a SCID mouse. (d-e) SEM images of tissues in vivo grown for 4 weeks.

Potentially, the large and open "valleys" on the coating can facilitate cellular activities [26,27]. A fluorescent optical microscope image of mesenchymal stem cells (MSC) after a one-day in vitro growth on the scaffold pre-coated with fibronectin (FIG. 10a) suggests a good compatibility between the cell and the scaffold. After 42 days, tissues formed (FIG. 10b) on the bioscaffold. On this basis, a Ti mesh tube about 5 mm wide and 10 mm long, pre-coated similarly, was implanted into severe combined immunodefficient (SCID) mice (FIG. 10c). After 4 weeks, the scaffold became fully covered by tissues (FIG. 10, d-e). The bioscaffold's nanoscale integrity has remained intact after the in vivo and in vitro tests.

This finding has demonstrated for the first time a generalized nanofabrication that involves simultaneously the solid-state "bottom-down", solution "top-up" and hierarchical self-assembly mechanisms, which is far beyond a newly reported preliminary work [28]. The NW-scaffold coating can be useful in important applications such as high-temperature heterogeneous catalysis, photocatalytic sterilization of surgical and food processing environments, solar energy conversion, bioseparation, bone replacement enriched with programmable release and weight support, to name a few.

Example 8

Controllable Release

The 3D macroporous structure has been found to be potentially useful in controlled release of drugs [29]. As shown in Table 2 and FIG. 5, the model drug's concentration reached a maximum after 6 hours of the release. The release was done by ~80% after the 2 hours, implying (i) a fast kinetics of drug release inside the scaffold macropores and (ii) the great potential for loading/releasing large proteins. Potentially, such 3D macroporous scaffolds of the bionanowires may accommodate drug molecules or protein promoters for precisely directing the growths of stem cells into different tissues at the same time within a confined environment [30,31]. It is believed that a further systematic optimization of the NW-scaffold pore size/structure, which is under an active investigation at present, could result in a plethora of new bioscaffolds that are capable of facilitating regenerations of different tissues and simultaneously releasing multi drugs on site over a prolonged time period in a programmable manner.

Table 2: Crystal violet released from nanowire scaffolds on Ti.

TABLE 2

| | Time (hours) | | | | |
|---|---|---|---|---|---|
| | 0 | 2 | 4 | 6 | 12 |
| Release (%) | 22.6 | 82.0 | 95.0 | 99.2 | 100 |

Materials and Methods for Example 9

Spinal Cord Injury Model

Experiments were carried out on male Sprauge Dawley rats that had received a on segment laminectomy over the T10-T11 segments. The rats were housed in a controlled ambient temperature (21±1° C.) facility with a 12 hour (h) light/dark schedule and had access to food and tap water ad libitum. All experiments were carried out according to the NIH Guidelines for animal handling and as approved by the local Institutional Ethics Committee.

Laminectomized rats were injured by making a longitudinal incision (about 1.5 mm deep and 5 mm long) over the right dorsal horn and the deepest part of the lesion was limited to the Rexed's lamina VIII. The animals were allowed to survive 5 h after injury. Laminectomized rats that did not receive injury were used as surgical controls, while non-laminectomized rats were used as negative controls.

Novel Compounds for Neuroprotection

Three novel compounds having anti-inflammatory and anti-edematous properties were chosen randomly from a large base of Acure Pharma synthesized neuroprotection compounds including AP-173, AP-713, and AP-364 (Acure Parma, Uppsala, Sweden). The compounds were dissolved in sterile water and administered separately at a dose of 1, 5, and 10 µg in 10 µl to the traumatized spinal cord 5 minutes after injury. Since initial observations indicated that the compounds administered at a concentration of 10 µg induced profound anti-edematous activity following injury, most of the experiments were performed using 10 µg doses of the compounds.

Nanowire Synthesis

Figure 11A:
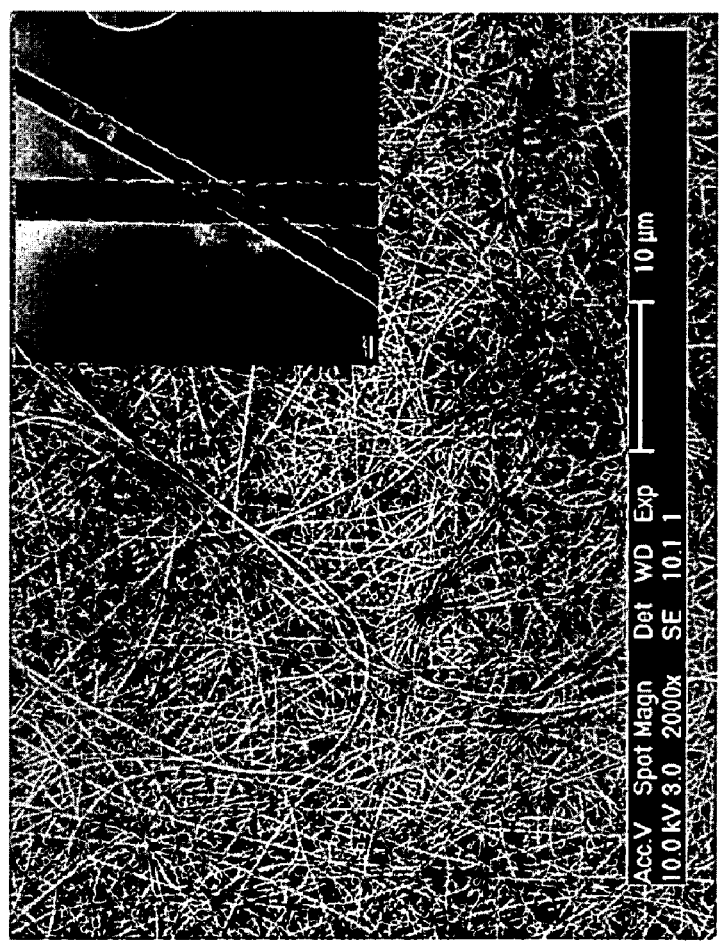
FIG. 11 depicts characteristics of nanowires used to deliver drugs to the central nervous system. (A) SEM and TEM characterizations of the nanowire film, showing an SEM photograph of the white, flexible assembled nanowire membrane and a TEM picture (inset) for confirming the nanowire morphology. (Scale bar: 50 nm). (B) X-ray powder diffraction pattern of titanate nanowire film. (C) An energy dispersive X-ray spectrum of the titanate nanowire membrane.
Figure 11B:
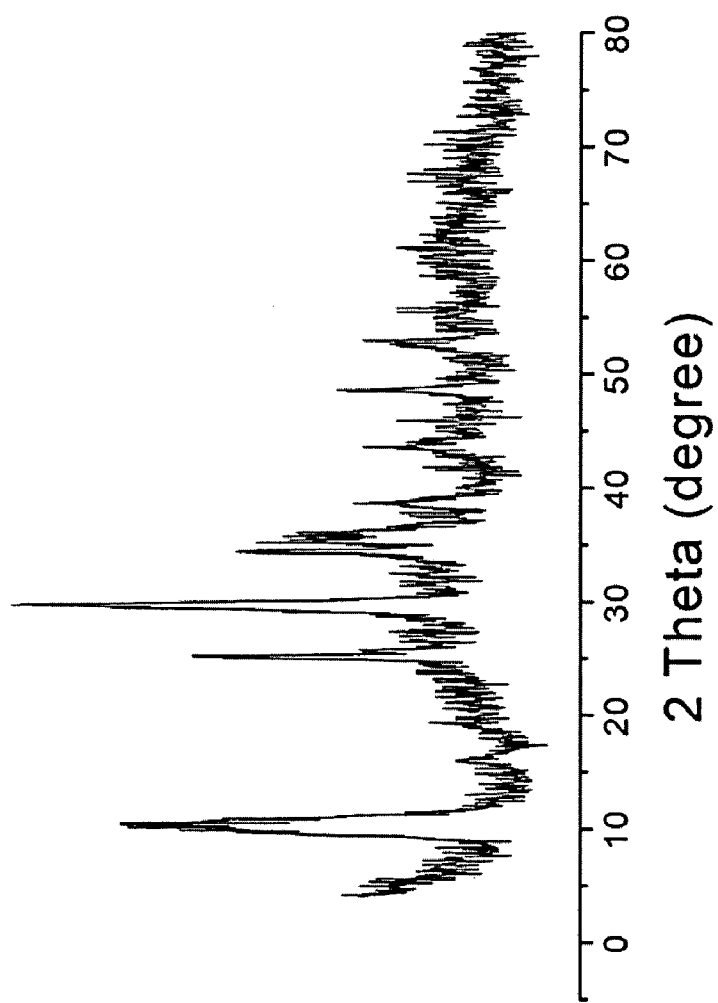
Figure 11C:
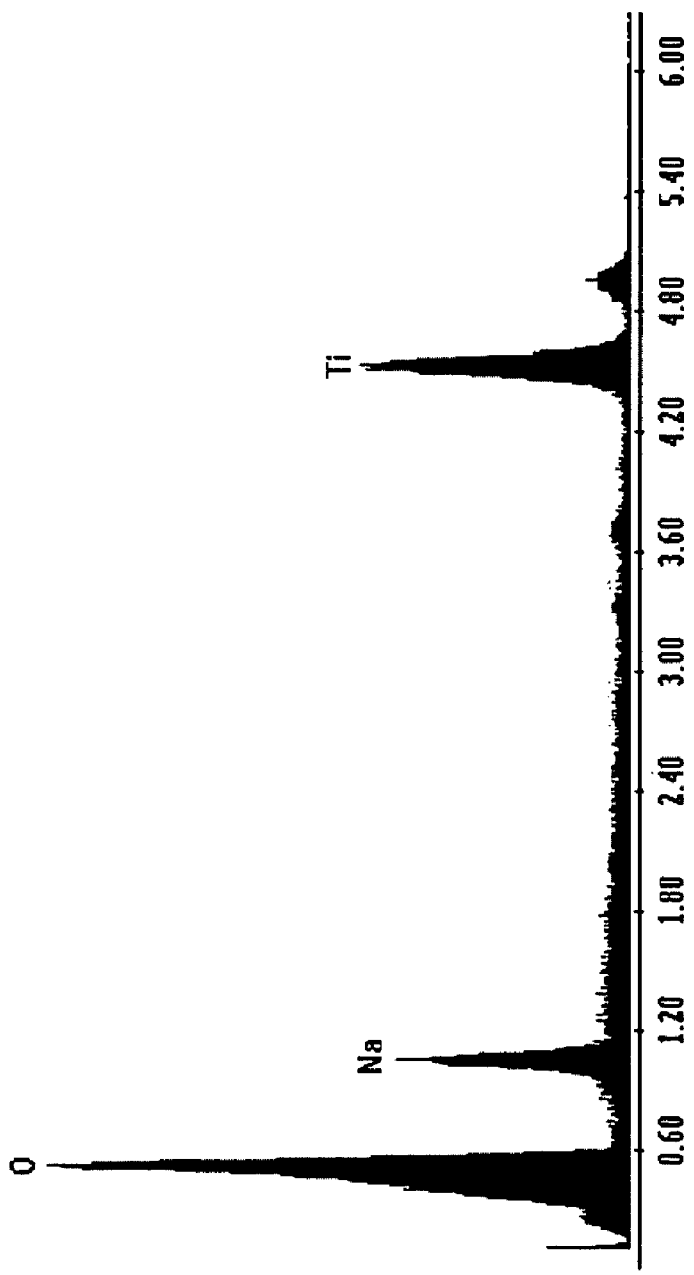

During the synthesis, 0.30 g of $TiO_2$ powder (Degussa P25) was added to 40 mL of 10 M alkali solution in a 150 mL Teflon-lined autoclave vessel. After a hydrothermal reaction for 7 days at a temperature above 160° C., long nanowires were collected and washed with distilled water or dilute acid. The nanowires were then fabricated into a flexible membrane on a Teflon template and allowed to dry at room temperature (FIG. 11A). X-ray diffraction patterns of the nanofibers (FIG. 11B) confirmed that the nanowire resembled the titanate lattice structure. The energy dispersive X-ray (EDX) elementary analysis clearly shows the existence of Ti, Na, and O in the nanowire membrane (FIG. 11C). The nanowires had a typical diameter ranging from 50 nm to 60 nm.

Tagging Nanowires with Compounds

The compounds AP-173, AP-713, and AP-364 were tagged separately onto the synthesized nanowires. The nanowire membrane was first sterilized in 0% ethanol and then rinsed in sterile 0.9% saline. The membrane (1.0 cm×1.0 cm) was then soaked in a 1.0 mL solution of 10 µg/L AP-173 or AP-713 at room temperature for 12 h. The compound soaked membrane was washed with deionized water before the use.

Functional Outcome Analysis

The functional outcome following spinal cord injury was measured using the Tarlov scale and inclined-plane angle tests as commonly known in the art. In brief, the Tarlov scale for hind limb function was assessed as 1=total paralysis, no sensation in the limb; 2=slight sensation in the limb after mild pinch, and can move the limb; 3=can place hind limb firmly on the platform and slight movement in the limb; 4=support weight on the hind limb and movement is sluggish; 5=walk with difficulty; and 6=normal walk. For the inclined plane test, animals were placed on an incline plane platform and the angle of the plane was adjusted as such that the animals could stay on the platform for 30 s without falling. Normal animals could stay on the platform at an angle of 60° without any problem. Spinal cord injured animals could not stay on the platform beyond the angle of 30°. Treatment with drugs can allow animals to stay between 30° and higher plane angles depending on the magnitude and duration of the neuroprotection.

Blood-Spinal Cord Barrier Permeability

The BSCB permeability was determined using Evans blue and [131]Iodine tracers that bound to serum proteins in vivo. Both protein tracers (Evans blue 2%, 0.3 ml/100 g; and [131] Iodine, 10 µCi/100 g body weight) were administered into the right femoral vein under anesthesia at the end of the experiment and the tracers were allowed to circulate for 5 minutes. The intravascular tracers were washed out by a brief saline perfusion (0.9% at 100 torr, for 45 seconds) through the heart and the spinal cord. Spinal cord segments T9 to T12 were dissected out and separated into T9, T10-11 and T12 segments. The separated segments were weighed and their radioactivity was determined using a gamma counter. Immediately before perfusion, a sample of whole blood was withdrawn from the left cardiac ventricle for the determination of whole blood radioactivity and/or Evans blue concentration. Leakage of radioiodine into the spinal cord was expressed as a percentage increase over the blood radioactivity. In some cases, after counting the radioactivity, the spinal cord samples were measured for Evans blue concentration using colorimetry.

Spinal Cord Edema Formation Detection

Spinal cord edema was determined using measurement of wet and dry weight of spinal cord samples in control, spinal cord inured, and drug-treated groups. The volume swelling (% ƒ) of the spinal cord was calculated from the differences between control and experimental spinal cord water content. Roughly, about a 1% increase in water content represents a 3% increase in volume swelling.

Spinal Cord Morphology

In a select group of control, spinal cord injured, and drug-treated groups, 4% buffered paraformaldehyde containing 0.1% glutaraldehyde and 0.25% picric acid was perfused immediately after saline perfusion (at 100 torr, about 150-250 mL each rat). After perfusion, the animals were wrapped with aluminum foil and kept overnight in a refrigerator at 4° C. The next day, identical tissue pieces from the spinal cord segments T9, T10-11, and T12 were dissected out and kept in the same fixative at 4° C. for 1 week. Small tissue sections (2 mm thick) were cut from each segment and embedded in paraffin for histological analysis. A few pieces were post-fixed in osmium and embedded in Epon for transmission electron microscopy. The paraffin sections (3 µm) were stained for Nissl and Haematoxylin and Eosin (H&E) and then examined using light microscopy for nerve cell, glial cell, and myelin damage. Small tissue pieces from the dorsal and ventral horn of Epon embedded spinal cord were processed for standard transmission electron microscopy.

Statistical Analyses

Quantitative data were analyzed using ANOVA followed by Dunnet's test for multiple group comparison from one control. The semiquantitative data were analyzed using a non-parametric Chi-Square test. P-values less than 0.05 were considered significant.

Example 9

Drug Delivery to the Spinal Cord by Tagged Nanowires Enhanced Neuroprotection and Functional Recovery Following Spinal Cord Injury Spinal cord injury (SCl) is a serious clinical situation for which very few therapeutic stratigies exist. SCl induces spinal cord cell and tissue injury that is progressive in nature. Damage to the microvasculature, breakdown of the blood-spinal cord barrier (BSCB), edema formation, and tissue destruction appear to be the main causes of long term disability of victims following SCl. Drug delivery to the spinal cord or brain following injury is a serious hindrance to therapy due to the blood-brain barrier and the blood-spinal cord barrier. Research has shown that topical application of drugs over the traumatized spinal cord results in enhanced neuroprotection compared to drug delivery through systemic circulation. With the onset of nano-technology, nanowires may provide an even better drug delivery strategy to the central nervous system.

The possibility that drugs attached to innocuous nanowires further enhanced their delivery and neuroprotective efficacy was examined using an in vivo rat spinal cord injury model. The focal SCl resulted in severe motor paralysis, widespread disruption of the BSCB to Evans blue albumin, [131]Iodine, or lanthanum tracers and exhibited profound edema formation. Cell and tissue destruction was present around the lesion site extending up to T8 through T12 segments. Topical application of AP-173, AP-713, and AP-364 in high quantity (10 µg in 20 µl) each markedly attenuated the behavioral dysfunction that was prominent around 2-3 hours after SCl. BSCB disruption, edema formation, and nerve cell, glial cell, and axonal injuries were less pronounced in drug treated injured animals. These beneficial effects were most significant in animals that received AP-713 treatment compared to AP-172 or AP-364 treatment. When these compounds were each tagged to TiO2-based nanowires, their beneficial effects on functional recovery and spinal cord pathology were further enhanced. Topical administration of nanowires alone did not influence trauma induced spinal cord pathology or motor functions. Taken together, the results indicated that the drug-delivery and their therapeutic efficacy were enhanced when the compounds were administered using nanowires.

Thus, in one aspect, the present invention relates to a synthetic nanostructure. In one embodiment, the synthetic nanostructure has a top region substantially comprising titanate nanowires, a middle region substantially comprising titanate nanoparticles and titanate nanowires, and a bottom region substantially comprising titanium, wherein some of the titanate nanowires of the top region are vertically rooted on the nanoparticles of the middle region. At least some of the titanate nanowires in the top region form 3D macroporous scaffolds with interconnected macropores.

In one embodiment, the bottom region comprises a titanium substrate that is selected from the group consisting of commercially pure titanium, a titanium alloy, and a titanium compound.

In one embodiment, the bottom region comprises a titanium substrate has morphology selected from the group consisting of foil, plate, wire, mesh, grid, sphere, and tube.

The nanowires have an average diameter ranging from about 10 nm to about 100 nm and an average length ranging from about 1 µm to about 1 mm.

The interconnected macropores have an average diameter ranging from about 2 to about 10 µm when the average nanowire length is about 5 µm.

The thickness of the middle region ranges from about 4 to about 30 µm.

The synthetic nanostructure further comprises a therapeutic molecule within one or more of the macropores.

In another aspect, the present invention relates to a process for preparing a synthetic nanostructure. In one embodiment, the process includes contacting a titanium substrate with a hydroxide solution, and hydrothermally heating the titanium substrate and the hydroxide solution to a temperature of not less than about 180° C. for a time sufficient to allow a plurality of nanowires to grow in the hydroxide solution both upwardly and downwardly, wherein some of the plurality of nanowires are vertically rooted on a plurality of nanoparticles formed a middle region between a top region comprising hydroxide solution and a bottom region comprising solid titanium. At least some of the titanate nanowires in the top region form 3D macroporous scaffolds with interconnected macropores.

The hydroxide solution is selected from the group consisting of potassium hydroxide and sodium hydroxide, wherein the concentration of sodium hydroxide is from about 0.2 mol/L to about 10.0 mol/L.

The titanium substrate and sodium hydroxide are hydrothermally heated at a temperature ranging from about 180° C. to about 250° C. for about 30 minutes to about 10 hours.

The average length of the nanowires, ranging from about 1 µm to about 1 mm, increases as at least one of the concentration of sodium hydroxide, the reaction time and the reaction temperature increases.

In yet another aspect, the present invention relates to a process for preparing a plurality of titanate nanowires. In one embodiment, the process includes contacting a substrate comprising titanium with a hydroxide solution, and hydrothermally heating the titanium substrate and the hydroxide solution to a temperature of not less than about 180° C. for a time sufficient to form a plurality of titanate nanowires. The plurality of titanate nanowires self assembles to form 3D macroporous scaffolds with interconnected macropores.

Some of the plurality of titanate nanowires are vertically rooted on a plurality of nanoparticles formed in a middle region between a top region comprising hydroxide solution and a bottom region comprising solid titanium, wherein the thickness of the middle region is about 4 µm after the hydrothermally heating step has proceeded about 30 minutes, about 10 µm after the reaction has proceeded about 2 hours, and about 20 µm after the reaction has proceeded about 4 hours, respectively.

In a further aspect, the present invention relates to a synthetic nanostructure. In one embodiment, the synthetic nanostructure has a plurality of titanate nanowires formed on a titanium substrate, wherein at least some of the plurality of titanate nanowires form 3D macroporous scaffolds with interconnected macropores.

The synthetic nanostructure has three regions, the regions comprising a top region substantially comprising titanate nanowires, a middle region substantially comprising titanate nanoparticles and titanate nanowires, and a bottom region substantially comprising titanium, wherein some of the titanate nanowires of the top region are vertically rooted on the nanoparticles of the middle region. The thickness of the middle region ranges from about 4 to about 30 µm.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

List Of References

1. Yaccoby S, Wezeman M J, Zangari M, Walker R, Cottler-Fox M, Gaddy D. 91:192-9.
2. Armstrong A R, Armstrong G, Canales J, Bruce P G. TiO2-B nanowires. Angew Chem Int Ed 43:2286-8.
3. Yoshida R, Suzuki Y, Yoshikawa S. J Solid State Chem 178:2179-85.
4. Yang J, Jin Z, Wang X, Li W, Zhang J, Zhang S, et al. Study on composition, structure and formation process of nanotube $Na_2Ti_2O_4(OH)_2$. Dalton Trans 20:3898-901.
5. Sun X, Li Y. Synthesis and characterization of ion-exchangeable titanate nanotubes. Chem-A Eur 9:2229-38.
6. Chen Q, Zhou W, Du G, Peng L-M. Trititanate nanotubes made via a single alkali treatment. Adv Mate 14:1208-11.
7. Spoerke E D, Stupp S I. Colonization of organoapatite-titanium mesh by preosteoblastic cells. J Biomed Mater Res A 3:960-9.
8. Hayashi K, Uenoyama K, Matsuguchi N, Sugioka Y. Quantitative analysis of in vivo tissue responses to titanium-oxide and hydroxyapatite-coated titanium alloy. Biomed Mater Res 25:515-23.
9. Suh J K, Matthew H W. Application of chitosan-based polysaccharide biomaterials in cartilage tissue engineering: a review. Biomaterials 21: 2589-98.
10. Zhang Y, Lim C T, Ramakrishna S, Huang Z M. Recent development of polymer nanofibers for biomedical and biotechnological applications. J Mater Sci Mater Med 16:933-46.
11. Brokx R D, Bisland S K, Gariepy J. Designing peptide-based scaffolds as drug delivery vehicles. J Control Release 78:115-23.
12. Silva G A, Czeisler C, Niece K L, Beniash E, Harrington D A, Kessler J A. Selective differentiation of neural progenitor cells by high-epitope density nanofibers. Science 303:1352-5.
13. Stevens M M, Marini R P, Schaefer D, Aronson J, Langer R, Shastri V P. In vivo engineering of organs: the bone bioreactor. Proc Natl Acad Sci USA 102:11450-5.
14. Mao, Y., Wong, S. S. J. Am. Chem. Soc. 2006, 128, 8217-8226.
15. Wu, D.; Liu, J.; Zhao, X.; Li, A.; Chen, Y.; Ming, N. Chem. Mater. 2006, 18, 547-553.
16. Chen, Q.; Du, G. H.; Zhang, S.; Peng, L. M. Acta Crystallogr., Sect. B 2002, 58, 587-593.
17. Yoshida, R.; Suzuki, Y.; Yoshikawa, S. J. Solid State Chem. 2005, 178, 2179-2185.
18. Izawa, H.; Kikkawa, S.; Koizumi, M. J. Phys. Chem. 1982, 86, 5023-5026.
19. Sun, Y.; Ndifor-Angwafor, N. G.; Riley, D. J.; Ashfold, M. N. R. Chem. Phys. Lett. 2006, 431, 352-357.
20. Kong, X-Y.; Ding, Y.; Yang, R.; Wang, Z. L. Science, 2004, 303, 1348-1351.
21. Feist, T. P.; Davies, P. K. J. Solid State Chem. 1992, 101, 275-95.
22. Andersson, S.; Wadsley, A. D. Acta Cryst. 1962, 15, 194-201.
23. Armstrong, A. R.; Armstrong, G.; Canales, J.; Bruce, P. G. Angew. Chem., Int. Ed., 2004, 43, 2286-2288.
24. Dong, W.; Cogbill, A.; Zhang, T.; Ghosh, S.; Tian, Z. R. J. Phys. Chem. B 2006, 110, 16819-16822.
25. Ibanez, J.; Litter, M.; Pizarro, R. J. Photochem. Photobiol. A 2003, 157, 81-85.
26. Zhang, Y.; Lim, C. T.; Ramakrishna, S.; Huang, Z. M. J. Mater. Sci.: Mater. Med. 2005, 16, 933-946.
27. Bhattarai, N.; Li, Z.; Edmondson, D.; Zhang, M. Adv. Mater. 2006, 18, 1463-1467.
28. Dong, W.; Zhang, T.; McDonald, M.; Padilla, C.; Epstein, J.; Tian, Z. R. Nanomedicine. 2006, 2, 248-252.
29. Brokx, R. D.; Bisland, S. K.; Gariepy, J. J. Controlled Release 2002, 78, 115-123.
30. Silva, G. A.; Czeisler, C.; Niece, K. L.; Beniash, E.; Harrington, D. A.; Kessler, J. A.; Stupp, S. I. Science 2004, 303, 1352-1355.
31. Stevens, M. M.; Marini, R. P.; Schaefer, D.; Aronson, J.; Langer, R.; Shastri, V. P. PNAS 2005, 102, 11450-11455.
32. Tuzlakoglu, K et al., J. Mater. Sci.: Mater. Med., (2005) 16:1099-1104.

What is claimed is:

1. A synthetic nanostructure, comprising:
   (a) a top region comprising titanate nanowires;
   (b) a middle region comprising titanate nanoparticles and titanate nanowires;
   (c) a bottom region comprising titanium and having a bottom surface,
   wherein the titanate nanowires are solid and are formed at a reaction temperature not less than about 180° C.,
   wherein the middle region is between the top region and the bottom region, and some of the titanate nanowires of the top region are substantially perpendicular to the bottom surface of the bottom region and extending into the middle region, and
   wherein some of the titanate nanowires in the middle region are vertically rooted on corresponding titanate nanoparticles and extend from the corresponding titanate nanoparticles in a downward direction that is substantially perpendicular to the bottom surface of the bottom region.

2. The synthetic nanostructure of claim 1, wherein at least some of the titanate nanowires in the top region form 3D macroporous scaffolds with interconnected macropores.

3. The synthetic nanostructure of claim 1, wherein the bottom region comprises a titanium substrate that is selected from the group consisting of commercially pure titanium, a titanium alloy, and a titanium compound, and wherein the bottom surface of the titanium substrate is the bottom surface of the bottom region.

4. The synthetic nanostructure of claim 1, wherein the bottom region comprises a titanium substrate having morphology selected from the group consisting of foil, plate, wire, mesh, grid, sphere, and tube, and wherein the bottom surface of the titanium substrate is the bottom surface of the bottom region.

5. The synthetic nanostructure of claim 1, wherein the titanate nanowires have an average diameter ranging from about 10 nm to about 100 nm and an average length ranging from about 1 μm to about 1 mm.

6. The synthetic nanostructure of claim 2, wherein the interconnected macropores have an average diameter ranging from about 2 to about 10 μm when the average nanowire length is about 5 μm.

7. The synthetic nanostructure of claim 1, wherein the thickness of the middle region ranges from about 4 to about 30 μm.

8. The synthetic nanostructure of claim 2, further comprising a therapeutic molecule within one or more of the macropores.

9. A synthetic nanostructure, comprising a plurality of titanate nanowires formed on a titanium substrate having a top surface and a bottom surface, wherein at least some of the plurality of titanate nanowires form 3D macroporous scaffolds with interconnected macropores, and further comprising three regions:
  (a) a top region comprising titanate nanowires;
  (b) a middle region comprising titanate nanoparticles and titanate nanowires; and
  (c) a bottom region comprising titanium,
    wherein the titanate nanowires are solid and formed at a reaction temperature not less than about 180° C.,
    wherein some of the titanate nanowires of the top region are extending into the middle region, and substantially perpendicular to the bottom surface of the titanium substrate, and
    wherein some of the titanate nanowires in the middle region are vertically rooted on corresponding titanate nanoparticles and extend from the corresponding titanate nanoparticles in a downward direction that is substantially perpendicular to the bottom surface of the titanium substrate.

10. The synthetic nanostructure of claim 9, wherein the titanium substrate is selected from the group consisting of commercially pure titanium, a titanium alloy, and a titanium compound.

11. The synthetic nanostructure of claim 9, wherein the titanium substrate has morphology selected from the group consisting of foil, plate, wire, mesh, grid, sphere, and tube, wherein the substrate may be any size.

12. The synthetic nanostructure of claim 9, wherein the titanate nanowires have an average diameter ranging from about 10 nm to about 100 nm and an average length ranging from about 1 μm to about 1 mm.

13. The synthetic nanostructure of claim 9, wherein the interconnected macropores have an average diameter ranging from about 2 to about 10 μm when the average nanowire length is about 5 μm.

14. The synthetic nanostructure of claim 9, wherein the thickness of the middle region ranges from about 4 to about 30 μm.

15. The synthetic nanostructure of claim 9, further comprising a therapeutic molecule, wherein the therapeutic molecule is substantially within the macropores.

* * * * *